United States Patent [19]

Ecker et al.

[11] Patent Number: 5,444,166
[45] Date of Patent: * Aug. 22, 1995

[54] CONSTITUTIVE TRIPLE RESPONSE GENE AND MUTATIONS

[75] Inventors: Joseph R. Ecker, Erial, N.J.; Joseph J. Kieber, Philadelphia, Pa.

[73] Assignee: Trustees of the University of Pennsylvania, Philadelphia, Pa.

[ * ] Notice: The portion of the term of this patent subsequent to Nov. 22, 2011 has been disclaimed.

[21] Appl. No.: 3,311

[22] Filed: Jan. 12, 1993

Related U.S. Application Data

[63] Continuation-in-part of Ser. No. 928,464, Aug. 10, 1992, Pat. No. 5,367,065.
[51] Int. Cl.$^6$ .................... C07H 17/00; A01H 5/00
[52] U.S. Cl. .................... 536/23.6; 800/205; 800/200; 800/230
[58] Field of Search .................. 800/205, 200, 230; 536/23.6

[56] References Cited

U.S. PATENT DOCUMENTS 5,073,676  12/1991  Bridges et al. .................. 800/205

OTHER PUBLICATIONS

Sambrook et al. Molecular Cloning: A Laboratory Manual, 2nd Ed., Cold Spring Harbor Laboratory Press, Cold Spring Harbor, N.Y. 1989.
Bleecker et al. 1988. Science 241:1086–1089.
Koncz et al. 1989. PNAS USA 86: 8467–8471.
Hanks et al. 1988. Science 241: 42–52.
Scott. 1990. Physiol. Plant. 78:147–152.
Guzman et al. 1990. Plant Cell 2:513–523.
Feldman et al. 1987 Mol. Gen. Genet. 208:1–9.
Harpham, N. V. J. et al., "The Effect of Ethylene on the Growth and Development of Wild-type and Mutant *Arabidopsis thaliana* (L.) Heynh", *Annals of Botany*, 68:55 (1991).
Boller, T., *The Plant Hormone Ethylene*, A. K. Mattoo and J. C. Suttle eds., 293–314 (1991), CRC Press, Inc. Boca Raton.
Yu, Y. et al., "Regulation of Auxin-induced Ethylene Production in Mung Bean Hypocotyls", *Plant Physiol.*, 63:589–590 (1979).
Guzman and Ecker, "Exploiting the Triple Response of Arabidopsis to Identify Ethylene-Related Mutatns", *The Plant Cell*, 2:513–5523 (1990).
Sato and Theologis, "Cloning the mRNA encoding 1-aminocyclopropane-1-carboxylate synthase, the key enzyme for ethylene biosynthesis in plants", *Proc. National Acad. Sci.*, 86:6621–6625, 1989.
Van Der Straeten et al., "Cloning and sequence of two different cDNAs encoding 1-aminocyclopropane-1-carboxylate synthase in tomato", *Proc. National Sci.*, 87:4859–4863, 1990.
Nakajima et al., "Molecular Cloning and Sequence of a Complementary DNA Encoding 1-Aminocyclopropane-1-carboxylate Synthase Induced by Tissue Wounding." *Plant Cell Physiol.*, 31(7):1021–1029, 1990.
Spanu et al., "Analysis and cloning of the ethylene-forming enzyme from tomato by functional expression of its mRNA in *Xenopus laevis* oocytes", *The EMBO Journal*, 10:2007–2013, 1991.
Blinder et al., "Constitutive Mutants in the Yeast Pheromone Response: Ordered Function of the Gene Products", *Cell*, 56: 479–486, Feb. 10, 1989.

*Primary Examiner*—David T. Fox
*Assistant Examiner*—Elizabeth C. Kemmerer
*Attorney, Agent, or Firm*—Woodcock, Washburn, Kurtz, Mackiewicz & Norris

[57] ABSTRACT

The present invention is directed to nucleic acid sequences for constitutive triple response mutants and corresponding amino acid sequences. Several ctr mutations are included within the scope of the present invention. The nucleic acid sequences set forth in SEQUENCE ID NUMBERS 1, and 3-6 as well as amino acid sequences set forth in SEQUENCE ID NUMBERS 1 and 2 are particular embodiments of the present invention.

9 Claims, 7 Drawing Sheets wt eto1 ctr1

Wild-type        ctr1

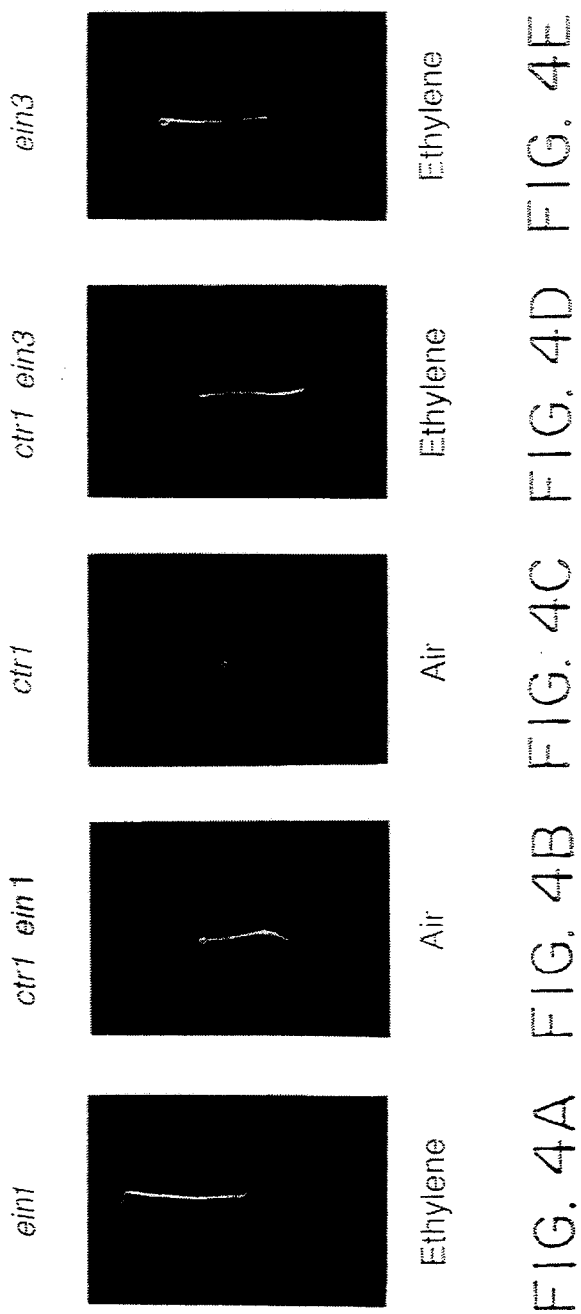

Wild Type — Wild Type + Ethylene — ctr1

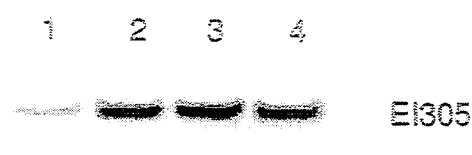
FIG. 6A
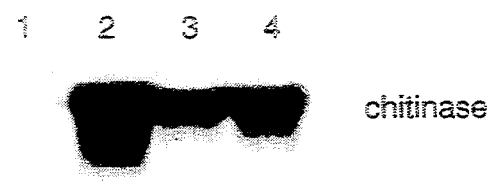
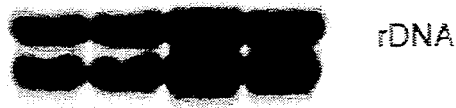
FIG. 6B

CONSTITUTIVE TRIPLE RESPONSE GENE AND MUTATIONS

REFERENCE TO GOVERNMENT GRANTS

This work was supported in part by research grants from the National Science Foundation, grant number DCB-9008323 and National Institutes of Health, grant numbers GM38894 and GM42471. The United States Government may have certain rights in this invention.

This application is a continuation-in-part of U.S. patent application Ser. No. 928,464, now U.S. Pat. No. 5,367,065, filed Aug. 10, 1992, the disclosures of which are hereby incorporated by reference in their entirety.

BACKGROUND OF THE INVENTION

Ethylene is one of five well-established plant hormones. It mediates a diverse array of plant responses including fruit ripening, leaf abscission and flower senescence.

The pathway for ethylene biosynthesis has been established (FIG. 1). Methionine is converted to ethylene with S-adenylmethionine (SAM) and 1-aminocyclopropane-1-carboxylic acid (ACC) as intermediates. The production of ACC from SAM is catalyzed by the enzyme ACC synthase. Physiological analysis has suggested that this is the key regulatory step in the pathway, (Kende, *Plant Physiol.*, 91:1–4 (1989). This enzyme has been cloned from several sources (Sato et al., *PNAS, (USA)* 86:6621 (1989); Van Der Straeten et al., *PNAS, (USA)* 87:4859–4863 (1990); Nakajima et al., *Plant Cell Physiol.* 29:989 (1990). The conversion of ACC to ethylene is catalyzed by ethylene forming enzyme (EFE), which has been recently cloned (Spanu et al., *EMBO J* 10:2007 (1991). Aminoethoxy-vinylglycine (AVG) and α-aminoisobutyric acid (AIB) have been shown to inhibit ACC synthase and EFE respectively. Ethylene binding is inhibited non-competitively by silver, and competitively by several compounds, the most effective of which is trans-cyclooctane. ACC synthase is encoded by a highly divergent gene family in tomato and Arabidopsis (Theologis, A., *Cell* 70:181 (1992)). ACC oxidase, which converts ACC to ethylene, is expressed constitutively in most tissues (Yang et al., *Ann. Rev. Plant Physiol.* 35:155 (1984)), but is induced during fruit ripening (Gray, 1992). It has been shown to be a dioxygenase belonging to the Fe2+/ascorbate oxidase superfamily (McGarvey et al., *Plant Physiol.* 98:554 (1992)).

Etiolated dicotyledonous seedlings are normally highly elongated and display an apical arch-shaped structure at the terminal part of the shoot axis; the apical hook. The effect of ethylene on dark grown seedlings, the triple response, was first described in peas by Neljubow in 1901, Neljubow, D., *Pflanzen Beih. Bot. Zentralb.* 10: 128 (1901). In Arabidopsis, a typical triple response consists of a shortening and radial swelling of the hypocotyl, an inhibition of root elongation and an exaggeration of the curvature of the apical hook (FIG. 2A). Etiolated morphology is dramatically altered by stress conditions which induce ethylene production the ethylene-induced "triple response" may provide the seedling with additional strength required for penetration of compact soils, see Harpham et al., *Annals of Bot.* 68:55 (1991). Ethylene may also be important for other stress responses. ACC synthase gene expression and ethylene production is induced by many types of biological and physical stress, such as wounding and pathogen infection, see Boller, T., in *The Plant Hormone Ethylene*, A. K. Mattoo and J. C. Suttle eds., 293–314 (1991), CRC Press, Inc. Boca Raton and Yu, Y. et al., *Plant Phys.* 63:589 (1979).

A collection of mutants affected in this response has been isolated. One class, the ein mutants (ethylene insensitive), are completely insensitive to ethylene. A second class of mutants are affected in only subset of the seeding responses. The hls1 mutant (hookless) completely lacks an apical hook either in the presence or absence of ethylene.

Constitutive hormone response mutants have been useful in elucidating mechanisms that underlie other hormone-mediated responses (e.g. yeast mating factor, Blinder et al., *Cell* 56:479 (1989)). Despite the information known about ethylene biosynthesis, how plants perceive and transduce hormone signals is almost completely unknown. While many of the components found in animal signal transduction chains have been found in plants, including kinases, and G proteins, no definitive correlation of these signal transducers with any hormone signal has been established. Elucidation of the complex role of these signal molecules would be greatly aided by the isolation of gene mutations which are affected in different steps in the signal transduction pathway.

The present invention addresses these important needs. A novel *Arabidopsis thaliana* mutant has been identified that constitutively exhibits seedling and adult ethylene responses in the absence of the hormone. The constitutive triple response (ctr) mutants display the "ethylene" phenotypes even in the presence of inhibitors of ethylene biosynthesis or receptor binding. ctr1 has a dramatically altered adult morphology that can be phenocopied in wild-type plants by growth in 1 ppm ethylene. Seedling and adult ctr1 plants show high-level constitutive expression of mRNAs for several ethylene inducible genes. Genetic, molecular and biochemical characterization of the CTR1 gene and protein product is set forth in the present invention. Genetic characterization of the interactions among modulatory components of the ethylene action pathway will provide insight into how plant hormones function. Thus, the quality, quantity and longevity of food, such as fruits and vegetables, and other plant products such as flowers, will be improved for market in both developed and undeveloped countries.

SUMMARY OF THE INVENTION

The present invention is directed to nucleic acid sequences for constitutive triple response, ctr, gene and corresponding amino acid sequence. Several ctr mutations, amino acid sequences and the corresponding protein products are included within the scope of the present invention. The nucleic acid sequences set forth in SEQUENCE ID NUMBERS 1, and 3–8 as well as amino acid sequences set forth in SEQUENCE ID NUMBERS 1 and 2 are particular embodiments of the present invention.

BRIEF DESCRIPTION OF THE FIGURES

FIG. 2D exhibits phenotypes of wild-type and ctr1 adult plants. Seeds were sown in soil and grown under continuous light at 22°-27° C. in individual pots for 18 days.

FIG. 4A-E display the double mutants constructed as described below. Seeds of wild-type and the mutants were plated and placed in the dark in chambers with air or in the presence of 10 μl C2H4/liter of air as indicated. After 72 hours representative seedlings were picked and photographed.

FIG. 5A shows a comparison of mutant and wild-type plants grown in air and 1 μl of C2H4/liter of air. Plants were grown as described. Representative individuals were picked and photographed. FIGS. 5B-D shows Nomarski microscopy of leaf epidermal cells. Individual leaves were excised from plants grown as described, fixed as described, and photographed under Nomarski optics. The leaf veins are visible as long streaks of light in the last two panels and the tip of a trichome is seen in top right of the middle panel. The doughnut-shaped stomata are also clearly visible.

FIGS. 6A-B display a Northern analysis of ethylene-regulated transcripts. FIG. 6A is a Northern blot of RNA isolated from three day-old etiolated wild-type (lanes 1 and 2) or mutant (lanes 3 and 4) seedlings grown in air (lanes 1 and 3) or 10 μl C2H4/liter of air (lanes 2 and 4). Twenty μg of total RNA was loaded in each lane and northern blots performed as described. The blot was probed pEI305, stripped and hybridized with an rDNA probe as a control for loading. FIG. 6B is a Northern blot of RNA isolated from 18 day-old wild-type (lanes 1 and 2) and ctr1 (lanes 2 and 4) adult plants grown under continuous light and then shifted for 48 hours to a chamber through which air (lanes 1 and 3) or 10 μl C2H4/liter of air (lanes 2 and 4) was passed. The gel was run and hybridized as above except 40 μg of total RNA was loaded and parallel blots were run rather than stripping one blot. One blot was hybridized with a chitinase probe and the second with an rDNA probe.

FIG. 7A is a Southern blot of genomic DNA. Five μg of genomic DNA from wild-type (lanes 1, 3, and 5) and the T-DNA insertional line ctr1-5 (lanes 2, 4, and 6) was digested with EcoRI (lanes 1 and 2), BamHI (lanes 3 and 4) or PvuII (lanes 5 and 6), electrophoresed through a 0.8% agarose gel, and blotted to a nylon membrane. The blot was hybridized as described with the insert from pCTG1, which contained the E. coli-rescued plant DNA from ctr1-5.

FIG. 7B is a northern blot of poly(A+) RNA. RNA was isolated from air-grown, adult wild-type (lane 1) or ctr1-5 (lane 2) and wild-type seedlings grown in air (lane 3) or 10 μl C2H4/liter of air (lane 4). Twenty μg of RNA was electrophoresed through a 1% agarose gel and blotted onto nylon membrane. The blot was hybridized to a cDNA insert containing the entire CTR1 coding region as described. The probe was then removed and the blot hybridized with DNA containing the entire coding region from the Arabidopsis topoisomerase I gene (TOP) (Kieber et al., 1992) to control for loading differences. Using size standards (Bethesda Research Laboratories), the CTR1 transcript was determined to be approximately 3.2 kb in size.

DETAILED DESCRIPTION OF THE INVENTION

Figure 1:
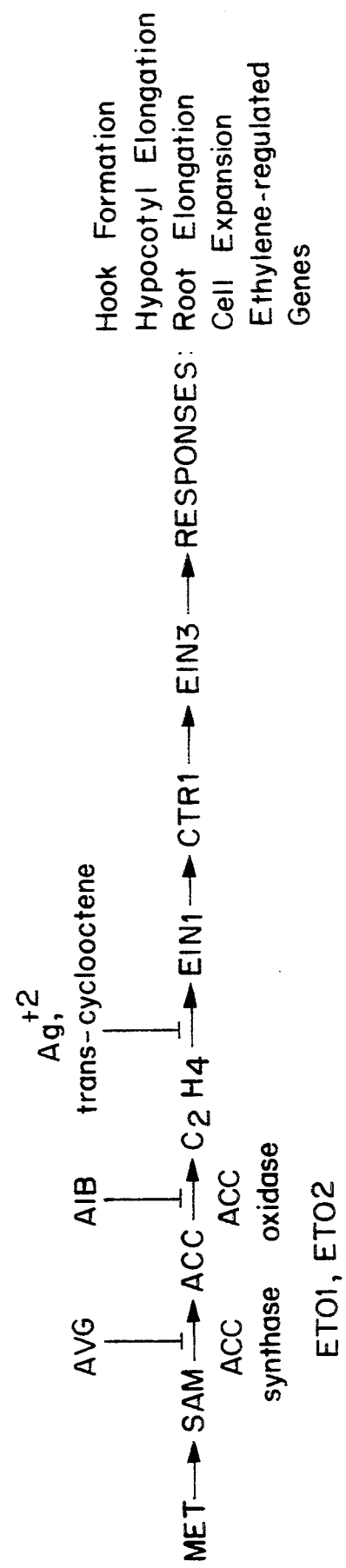
FIG. 1 is a schematic illustration of the ethylene biosynthetic pathway.

The present invention is directed to constitutive triple response, ctr, nucleic acid sequences and corresponding amino acid sequences. In accordance with the present invention, the CTR gene is identified. Several ctr mutations are included within the scope of the present invention. The nucleic acid sequences set forth in SEQUENCE ID NUMBERS 1, and 3-7 as well as amino acid sequences set forth in SEQUENCE ID NUMBERS 1 and 2 are particular embodiments of the present invention.

Specifically, SEQUENCE ID NO: 1, the isolated cDNA representing the nucleic acid sequence coding for CTR and the isolated genomic CTR DNA sequence of SEQUENCE ID NO: 3 are particularly preferred embodiments of the invention. The purified amino acid sequence of SEQUENCE ID NUMBERS 1 and 2 represent the CTR protein product encoded by the cDNA identified above. The ctr1-2 mutation set forth in SEQUENCE ID NO: 4 has a 17 base pair deletion, beginning at nucleotide position 1995 of CTR genomic DNA sequence, corresponding to the position 2770 in SEQUENCE ID NO: 3. The ctr1-2 mutation of SEQUENCE ID NO: 4 was generated by x-ray mutagenesis. The ctr1-3 mutation set forth in SEQUENCE ID NO: 5 has a "C" to "T" point mutation resulting in a stop codon at position 1927 of CTR genomic DNA sequence, corresponding to position 2702 in SEQUENCE ID NO: 3. The ctr1-3 mutation of SEQUENCE ID NO: 5 was generated by EMS mutagenesis. In the resulting protein product, "arg" is converted to a stop signal. The ctr1-1 mutation set forth in SEQUENCE ID NO: 6 has a "T" to "A" point mutation at nucleotide position 3295 of CTR genomic DNA sequence, corresponding to the position 4800 in SEQUENCE ID NO: 3. The ctr1-1 mutation of SEQUENCE ID NO: 6 was generated by DEB mutagenesis. Another mutation, ctr1-4, see SEQUENCE ID NO: 7, was generated by EMS mutagenesis and has a "G" to "A" transition at position 3233, corresponding to position 4008 of SEQUENCE ID NO: 3 that is predicted to result in a "Glu" to "Lys" change at amino acid 596, another invariant residue in all kinase catalytic domains. ctr1-5 comprises a T-DNA insertion at position 3041 in intron 7 of CTR genomic DNA sequence wherein 25 base pairs were deleted from the left border of the T-DNA at the junction with plant DNA.

In accordance with the present invention, nucleic acid sequences include and are not limited to DNA, including and not limited to cDNA and genomic DNA; RNA, including and not limited to mRNA and tRNA; and suitable nucleic acid sequences such as those set forth in SEQUENCE ID NOS: 1, and 3-6, and alterations in the nucleic acid sequences including alterations, deletions, mutations and homologs.

Also amino acid, peptide and protein sequences within the scope of the present invention include, and are not limited to the sequence set forth in SEQUENCE ID NO: 2, the amino acid sequences corresponding to nucleic acids in SEQUENCE ID NOS: 1 and 3-6, and alterations in the amino acid sequences including alterations, deletions, mutations and homologs.

In accordance with the invention, the CTR and ctr nucleic acid sequences employed in the invention may be exogenous sequences. Exogenous, as used herein, denoted a nucleic acid sequence which is not obtained from and would not normally form a part of the genetic make-up of the plant or the cell to be transformed, in its untransformed state. Plants comprising exogenous nucleic acid sequences of CTR or ctr mutations, such as and not limited to the nucleic acid sequences of SEQUENCE ID NUMBERS: 1 and 3-6 are within the scope of the invention.

Transformed plant cells comprising nucleic acid sequences of CTR or ctr mutations, such as and not limited to the nucleic acid sequences of SEQUENCE ID NUMBERS: 1 and 3-6, are within the scope of the invention. Transformed cells of the invention may be prepared by employing standard transformation techniques and procedures as set forth in Sambrook et al., *Molecular Cloning: A Laboratory Manual*, 2nd ed., Cold Spring Harbor Laboratory Press, Cold Spring Harbor, N.Y. (1989).

The action of the plant hormone ethylene utilizing the "triple response" of *Arabidopsis thaliana* was studied. The "triple response" in Arabidopsis consists of three distinct morphological changes in dark-grown seedlings upon exposure to ethylene: inhibition of hypocotyl and root elongation, radial swelling of the stem and exaggeration of the apical hook. A class of constitutive mutants, ctr, display a constitutive triple response in the presence of ethylene biosynthetic inhibitors, and is most likely affected at, or downstream of the receptor. Based on the results of genetic experiments, overexpression of the normal or truncated versions of the negative regulatory gene CTR1 in transgenic plants would be predicted to result in a dominant ethylene-insensitive phenotype.

Several ctr alleles have been identified, ctr1-1 to ctr1-5. ctr1 mutants are recessive, do not produce elevated levels of ethylene and have a dramatically altered seedling and adult morphology. The adult phenotype of ctr1 can be phenocopied by growth of wild-type plants in the presence of 1 ppm ethylene and is shown to result, at least in part, to a reduction in cell size.

The present invention is directed to a method of inducing a constitutive triple response in wild-type plants by growing the wild-type plants in the presence of from about 1 ppm to about 10 ppm ethylene for about 2 weeks to about 3 weeks.

At the molecular, cellular and whole plant level, and in seedling and adult plants, air-grown ctr1 mutants strongly resemble ethylene-treated wild-type plants. The recessive nature of ctr suggests that the ethylene-response pathway is normally under negative regulation and loss of function of the CTR repressing activity results in a constitutive triple response phenotype.

The gene corresponding to CTR has been cloned as set forth below and the sequence of cDNA clone is described. The gene encodes a protein that resembles the Raf family of serine/threonine kinases. Physiological, biochemical and genetic evidence indicates that the CTR1 and EIN3 gene products are required for transduction of the ethylene signal in both etiolated seedling and adult plants. The putative CTR1 kinase is postulated to act as a negative regulator in the ethylene signal transduction chain.

Also disclosed herein is a recessive mutation referred to as ein3 which causes insensitivity to ethylene whereas ctr1 results in constitutive activation of all known ethylene responses in the absence of ethylene. EIN3 may act as a positive regulator whereas CTR1 gene product appears to act as a negative regulator in the ethylene action pathway. The predicted protein sequence of EIN3 and EIL1, an EIN3 related gene, are reminiscent of transcription factors. These include acidic and basic domains and mono-amino acid repeat motifs. The EIN3 and EIL1 proteins may be targets for phosphorylation by the CTR1 kinase. Double mutant analysis indicated that the EIN3 gene product acts downstream of the CTR1 gene product in the ethylene signal transduction pathway. CTR1, in turn, acts downstream of EIN2 and EIN1/ETR1.

In accordance with the present invention, the present plants included within the scope of the present invention are higher and lower plants of the Plant Kingdom. Mature plants and seedlings are included in the scope of the invention. A mature plant includes a plant at any stage in development beyond the seedling. A seedling is a very young, immature plant in the early stages of development.

Transgenic plants are included within the scope of the present invention which have a phenotype characterized by the CTR gene or ctr mutations. Particularly preferred plants are those from: the Family Umbelliferae, particularly of the genera Daucus (particularly the species *carota*, carrot) and Apium (particularly the species *graveolens dulce*, celery) and the like; the Family Solanacea, particularly of the genus Lycopersicon, particularly the species *esculentum* (tomato) and the genus Solanum, particularly the species *tuberosum* (potato) and *melongena* (eggplant), and the like, and the genus Capsicum, particularly the species *annum* (pepper) and the like; and the Family Leguminosae, particularly the genus Glycine, particularly the species *max* (soybean) and the like; and the Family Cruciferae, particularly of the genus Brassica, particularly the species *campestris* (turnip), *oleracea* cv Tastie (cabbage), *oleracea* cv Snowball Y (cauliflower) and *oleracea* cv Emperor (broccoli) and the like; the Family Compositae, particularly the genus Lactuca, and the species *sativa* (lettuce), and the genus Arabidopsis, particularly the species *thaliana* (Thale cress) and the like. Of these Families, the most preferred are the leafy vegetables, for example, the Family Cruciferae, especially the genus Arabidopsis, most especially the species *thaliana*.

The present invention will benefit plants in relation to stress. Stress includes, and is not limited to, infection as a result of pathogens such as bacteria, viruses, fungi; wound healing and soil penetration. Bacterial infections include, and are not limited to, *Clavibacter michiganense* (formerly *Coynebacterium michiganense*), *Pseudomonas solanacearum* and *Erwinia stewartii*, and more particularly, *Xanthomonas campestris* (specifically pathovars campestris and vesicatoria), *Pseudomonas syringae* (specifically pathovars tomato, maculicola).

In addition to bacterial infections, other examples plant viral and fungal pathogens within the scope of the invention include and are not limited to, tobacco mosaic virus, cauliflower mosaic virus, turnip crinkle virus, turnip yellow mosaic virus; fungi including *Phytophthora infestans, Peronospora parasitica, Rhizoctonia solani, Botrytis cinerea, Phoma lingam (Leptosphaeria maculans)*, and *Albugo candida*.

The present invention is further described in the following examples. These examples are not to be construed as limiting the scope of the appended claims.

EXAMPLE 1

Isolation of Constitutive Mutants

Independent lots of ethyl methanesulfonate (EMS), diepoxybutane (DEB) and X-ray mutagenized seeds were screened for mutants that constitutively display the triple response by plating on agar in the absence of added ethylene in the dark, see Table 1. A total of greater than $10^6$ seedlings were screened in this manner, yielding 400 putative mutants, of which 18 mutants survived and produced seeds. These 18 were retested for this phenotype.

*Arabidopsis thaliana* ecotype Columbia was the parent strain for mutant isolation, with the exception of the T-DNA tagged allele which was isolated from a population developed by Feldman and Marks in the Wassilewskija ecotype. Feldman et al., *Mol. Gen. Genet.* 208:1 (1987) and Feldman, K. A., *Plant Journal* 1:71 (1991). Marker lines were obtained from the Arabidopsis Biological Resource Center, Ohio State University, and were as follows: W11 lu tt3; W13 ttg yi; NW85 tt4. Triple response screens were performed on petri plates as described by Guzman et al., The *Plant Cell* 2:513 (1990). The following concentrations of inhibitors were used: AVG (10 μM), AgNO$_3$ (17 μg/ml), AIB (2 mM) and trans-cyclooctene (90 μl gas/liter of air). EMS mutagenized seeds were obtained as described by Guzman et al., supra. For X-ray mutagenesis, hydrated seeds were treated with 20,000 rads (30 cm from the source for 43 minutes using a 2mA1 filter at the Hospital of the University of Pennsylvania) and then grown as 20 independent lots; 1,500 plants per 35 cm×45 cm tub. For the diepoxybutane, DEB, mutagenesis, seeds were soaked in water overnight, then soaked in 22 mM DEB for 4 hours, washed extensively and grown in 20 independent lots as above. Plants were generally grown in Metro-Mix TM 200 (Grace) in continuous illumination with fluorescent light at 25° C. and watered with a 15-16-17 (Nitrogen-phosphorous-potassium) nutrient solution, also known as Peter's lite, every fourth watering.

For growth of adult plants in ethylene, seeds were sown in 6" pots in Metro-Mix TM and placed in the growth room in chambers sealed with tape. Hydrocarbon-free air or 1 μl C2H4/liter of air was continuously passed through the chamber at a flow rate of approximately 40 ml/min.

Figure 2A:
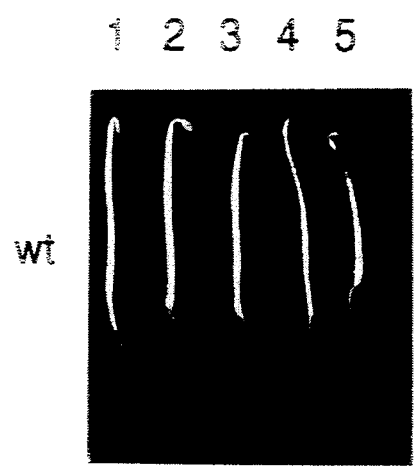
FIGS. 2A-2D exhibits the phenotypes of Arabidopsis seedlings. Surface-sterilized seeds were plated on growth medium and cold treated for four days (4° C.) before germination and growth in the dark at 23° C. for 72 hours. The wild-type (FIG. 2A), ctr1 (FIG. 2C) and eto1 (FIG. 2B) controls seedlings were grown in 1) no inhibitor, 2) AVG, 3) AIB, 4) AgNO3 and 5) transcyclooctene. Representative seedlings are shown, except the AVG-treated wild-type seedling in which the root was broken prior to photography.
Figure 2B:
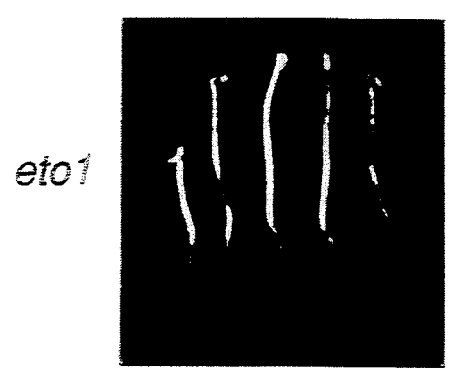

Several inhibitors of ethylene biosynthesis and binding have been described (FIG. 1), and these were examined for their ability to revert the constitutive phenotype of these mutants. Aminoethoxyvinylglycine (AVG), an effective inhibitor of pyridoxal phosphate-mediated enzyme reactions, inhibits ACC synthase, the penultimate step in ethylene biosynthesis which converts S-adenyl-methionine (SAM) to 1-aminocyclopropane-l-carboxylic acid (ACC). α-aminoisobutyric acid (AIB), a structural analog of ACC, has been shown to competitively inhibit the formation of ethylene from ACC, and thus block ACC oxidase. Satoh et al., *Physiol. Plant.* 5:521 (1983) and Yang et al., supra. Trans-cyclooctene has been shown to be an extremely effective competitive inhibitor of ethylene binding, and silver ion has been shown to be a potent non-competitively inhibitor of ethylene action in several classic ethylene responses. Beyer, Jr., E. M., *Plant Physiol* 58:268 (1976) and Sisler et al., *Plant Growth Reg.* 9:157 (1990). The mutants fell into two classes, those in which the constitutive triple response phenotype was efficiently reverted by all four inhibitors, class 1 (FIG. 2A) and those that were completely unaffected by all four compounds, class 2 (FIG. 2A). This strongly suggested that the constitutive triple response phenotype of the first class was due to an over-production of ethylene, whereas the second class was affected in the perception of ethylene. Measurements of ethylene production confirmed that all the class 1 mutant seedlings, which included the previously identified eto1 mutation, did over-produce ethylene.

All of the recessive Eto mutants failed to complement eto1-1. Three additional dominant Eto mutations were identified. The eto2 mutation was completely dominant (Table 1), produced twenty-fold more ethylene than wild-type seedlings and mapped to the bottom of chromosome 5, close to the yi mutation (2.2±0.8 cM). The eto3 mutation was also completely dominant, produced 100-fold more ethylene than wild-type seedlings and may be allelic to eto2. All Eto adult plants produced thee same or only slightly more ethylene than wild-type adults, which suggests that perhaps the production of ethylene is regulated by independent pathways in seedling and adult plants or in light and dark grown plants. Alternatively, a negative feedback mechanism may repress excess ethylene production in adult Eto mutants.

Figure 3:
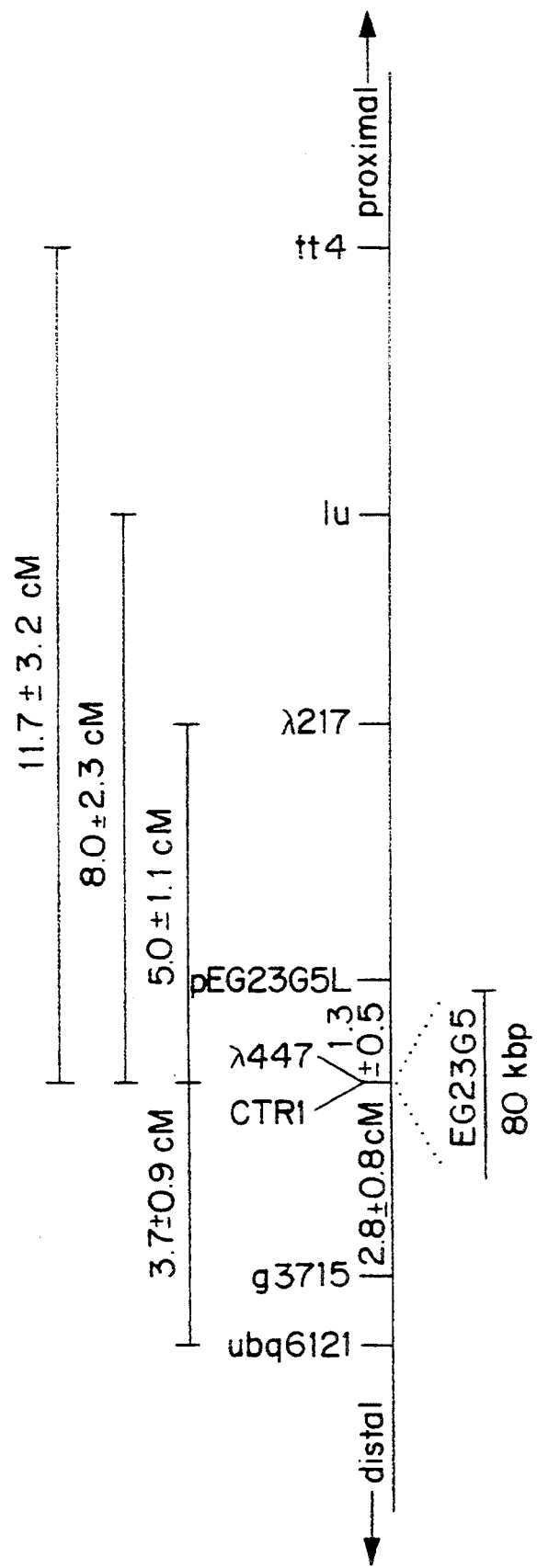
FIG. 3 displays the genomic region corresponding to the top of chromosome 5, with proximal and distal referring to the orientation on the chromosome. The genetic distance (in cM) between two mapped markers is indicated above the given interval, plus or minus the standard error. The morphological markers lu and tt4 were mapped relative to the ctr1 mutation. Shown below the map is the position of pEG23G5L, a left end rescue from the YAC EG23G5 (Grill and Somerville, 1991). CTR1 and λ447 are contained within this YAC and several other clones (not shown) as indicated by the dotted lines. A recombinant inbred (RI) population was used to map RFLPs detected by CTR1, pEG23G5L, g3715, λ271 and ubq6121.
Figure 5A:
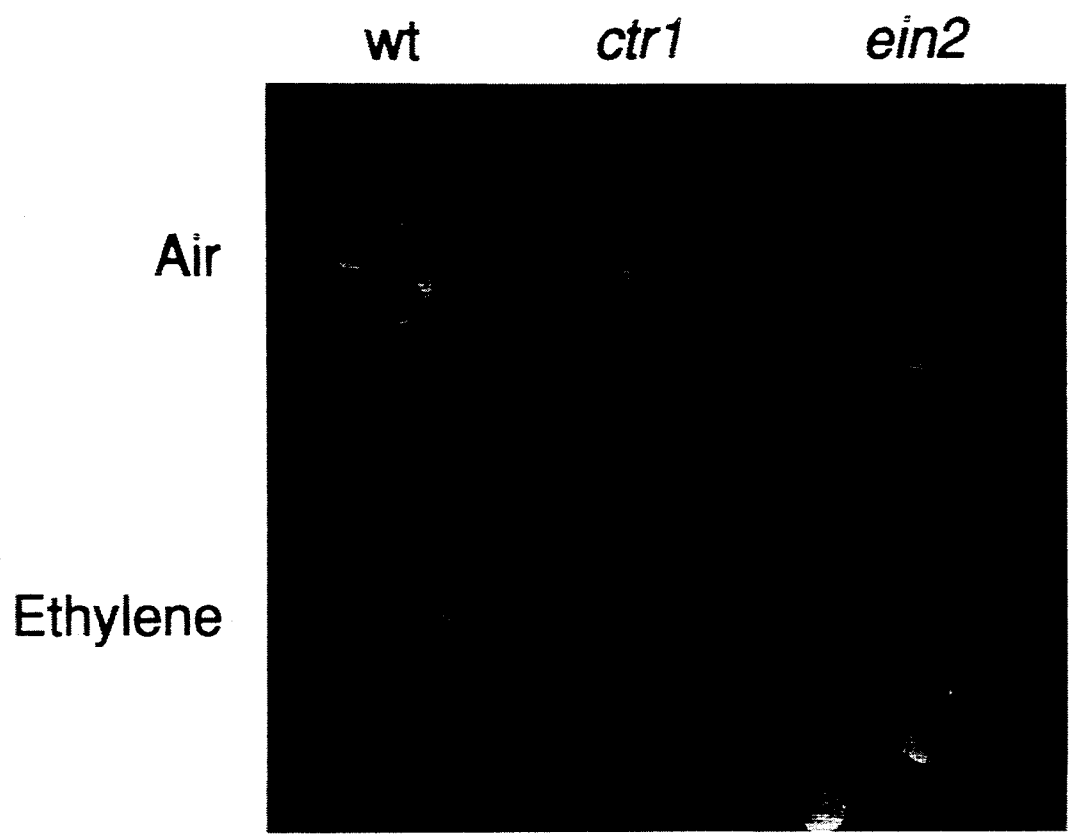
FIG. 5A-D display the effects of ethylene on leaf morphology and cell size.
Figures 5B, 5C, 5D:

All of the class 2 mutants fell into one complementation group, ctr1. Neither ctr1 seedlings nor adult plants produced significantly more ethylene than wild-type plants. The ctr1 mutation is recessive and segregates in a manner most consistent with a single Mendelian gene, although it differs significantly from the expected 3:1 ratio as judged by chi-square analysis (Table 1). The altered segregation ratio (4.8 wild-type: 1 ctr1) is most likely due to a decrease in transmission of the ctr1 allele relative to wild-type, which may result from such factors as a decrease in gametophyte viability or pollen tube growth rate. The mutation was mapped using visible markers to the top of chromosome 5, close to tt4 and lu mutations (FIG. 3). Using restriction fragment length polymorphism (RFLP) markers, close linkage was detected with the RFLPs λ447 and ubq6121 on chromosome 5 (FIG. 3). No recombinants were observed between λ447 and the ctr1 mutation (out of 86 chromosomes) in an F2 mapping population generated from a cross of ctr1 (ecotype Columbia) to a wild-type plant of the Niederzenz ecotype.

EXAMPLE 2

Genetic Analysis of Mutants

Crosses were performed as described Guzman and Ecker, supra. RFLP analysis was performed by crossing ctr1-1 (Columbia background) to a wild-type plant of the Niederzenz ecotype. Individual F3 families were grown and DNA isolated by CsCl banding. The restriction patterns of DNA hybridizing to the RFLP probes from each of the F3 families was analyzed by Southern blotting. DNA probes were prepared by random hexamer labeling.

The cloned CTR1 gene was mapped relative to the RFLP markers ubq6121, λ217 and g3715 using recombinant inbred lines (kindly provided by Caroline Dean, John Innes Institute, Norwich, U.K.) and distances calculated using RI plant Manager program v2.2 developed by Kenneth Manly (Buffalo, N.Y.). YACs were screened with CTR1 and λ447 and the ends rescued as described in Matallana et al., Methods in Arabidopsis Research, Koncz et al., Eds., Singapore: World Scientific, pgs 144–169 (1992).

TABLE 1

Genetic Analysis of Constitutive Triple Response Mutants

| Cross[a] | Type | Total | Constitutive Triple Res.[b] + | Constitutive Triple Res.[b] − | $X^{2c}$ |
|---|---|---|---|---|---|
| ctr1-1/ctr1-1 X CTR1/CTR1 (DEB)[d] | F1 F2 | 75 1924 | 0 333 (4.8:1) | 75 1591 | 60.7 p < .05 |
| ctr1-2/ctr1-2 X CTR1/CTR1 (X-ray) | F1 F2 | 62 264 | 0 45 (4.9:1) | 62 219 | 8.9 p < .05 |
| ctr1-1/ctr1-1 X ctr1-2/ctr1-2 (X-ray) | F1 | 13 | 13 | 0 | |
| ctr1-1/ctr1-1 X ctr1-3/ctr1-3 (EMS) | F1 | 16 | 16 | 0 | |
| ctr1-1/ctr1-1 X ctr1-4/ctr1-4 (EMS) | F1 | 11 | 11 | 0 | |
| ctr1-1/ctr1-1 X ctr1-5/ctr1-5 (T-DNA) | F1 | 28 | 28 | 0 | |
| ETO2/ETO2 X eto2/eto2 (DEB) | F1 F2 | 17 578 | 17 422 | 0 156 | 1.2 p > 0.1 |
| ETO3/ETO3 X eto3/eto3 (DEB) | F1 | 36 | 36 | 0 | |

[a]Crosses were performed as described in Experimental Procedures.
[b]Seedlings were scored for the triple response in the absence of ethylene as described in Experimental Procedures.
[c]Chi-square was calculated for an expected 3:1 ratio.
[d]Parenthesis indicate mutagen used to generate allele. 61.5

The epistatic relationships between ctr1 and several mutations that result in insensitivity to ethylene (EIN) was examined. ein1 is a single gene, dominant mutation that results in insensitivity to ethylene in both seedlings and adult plants. ein3 is a second, recessive mutation that has a somewhat weaker ethylene-insensitive phenotype. Crosses were carried out between ctr1, ein1 and ein3. The double mutants were identified and their seedling (FIGS. 4A–E) and adult phenotypes examined.

Double mutants were constructed by crossing the two parents and collecting seeds from individual F1 plants. The F2 seeds were plated in air and ethylene in the dark, Guzman et al., supra and seedlings corresponding to each parental phenotype were picked and grown. These F2 individuals were progeny-tested by collecting and then plating their seeds in air and ethylene. Putative double mutants were grown and their genotype tested by crossing to wild-type to examine for segregation of the two parental phenotypes.

The double mutants were identified and their seedling and adult phenotypes examined. The ctr1 ein1 double mutant displayed the constitutive ethylene phenotypes, see FIGS. 4A–E, whereas the ctr1 ein3 double mutant showed an ethylene-insensitive phenotype. These results suggest that the CTR1 gene product acts at, or downstream of the ein1 gene product, and at or upstream of the EIN3 gene product in the ethylene signal transduction chain, FIG. 1.

EXAMPLE 3

Ethylene-Induced Genes are Constitutively on in the ctr1 Mutant

The steady state level of several ethylene-induced transcripts was examined in both seedlings and mature ctr1 plants. EI305 is a random transcript that was isolated by differential screening of ethylene and air treated seedlings. The basic chitinase gene and β 1,3 glucanase genes have been shown to be induced by ethylene in adult plants.

Seeds were sterilized and one mg per plate (150 mm) was plated. Seedlings were grown in the dark with either hydrocarbon free air or 10 μl $C_2H_4$/l of air blowing through at approximately 60 ml/minute for 48 hours. Seedlings were harvested by pouring liquid nitrogen on the plate and then scraping the frozen seedlings into liquid nitrogen. Adult plants were grown in growth chambers until just beginning to bolt, and moved to chambers through which air or 10 μl $C_2H_4$/liter of air was blowing at approximately 60 ml/minute for 48 hours. The aerial portions of the plants were harvested into liquid nitrogen and stored at −70° C. until use. Total RNA was prepared by extraction with phenol/chloroform, polyA RNA isolated by oligoT-cellulose affinity columns and Northern analysis was as described by Sambrook, et al., *Molecular Cloning: A Laboratory Manual*, 2nd ed., Cold Spring Harbor Laboratory Press, Cold Spring Harbor, N.Y. (1989). For size markers, a RNA ladder from Bethesda Research Labs was used.

Results of the Northern analysis demonstrated that the steady state level of these ethylene-regulated genes was dramatically increased in air-grown ctr1 seedlings or adult plants, see FIGS. 6A and B. The steady state level of EI305 in air-grown ctr1 seedlings is comparable to wild-type plants grown in 10 μl $C_2H_4$/liter of air. The basic chitinase gene is also elevated in ctr1 adults, but not to as high a level as ethylene-treated wild-type plants. This may be due to the fact that the wild-type plants are grown in air, then shifted to ethylene, whereas the ctr1 mutants may be acting like plants treated continuously with ethylene.

EXAMPLE 4

Cloning the CTR1 Gene

The CTR1 was mapped to an interval between two RFLPs on the top of chromosome 5 (FIG. 3) and a chromosome walk in this area was initiated using the yUP yeast artificial chromosome (YAC) library. In parallel, a T-DNA insertional library was screened for Ctr mutants and a single line was found out of a total of 1/13,000 screened that segregated for the constitutive triple response phenotype and failed to complement ctr1-1. Genetic analysis showed that the Km$^r$ marker on the T-DNA was very closely linked to the ctr1 mutation in this line (Table 2). The T-DNA insertion was very complex; a left border fragment detects greater than seven distinct bands in a Southern blot. The neomycin phosphotransferase (NTPII; kanamycin resistance gene from the T-DNA insert of ctr1-5 segregated at a 3:1 ratio (Km$^r$:Km$^s$) in progeny from a heterozygous parent. The NPTII gene within the T-DNA was mapped relative to ctr1 in this line. Seedlings from a population segregating for the Ctr phenotype were screened for kanamycin resistance. Seedlings that displayed the Ctr phenotype were isolated and all (1131) were found to be resistant to kanamycin. Wild-type progeny that were resistant to kanamycin were also isolated and progeny-tested for the ctr1 mutation. Of the 256 lines examined, all but a single line segregated for ctr1. Souther blot analysis suggests that this line has undergone a rearrangement of the T-DNA which may lead to efficient splicing of the intron in which the insertion resides. Taken together, these results indicate that the T-DNA was very closely linked to the ctr1 mutation in this line (<1.1 cM at 95% confidence). The plant DNA flanking the site of insertion was isolated by plasmid rescue of the left border of the T-DNA.

DNA from a T3 population that was segregating for ctr1-5 was prepared by CsCl purification as described by Sambrook et al., *Molecular Cloning: A Laboratory Manual*, 2nd ed., Cold Spring Harbor Laboratory Press, Cold Spring Harbor, N.Y. (1989) and 5 μg was digested with SalI restriction enzyme. This was extracted once with an equal volume of phenol/CHCl$_3$/isoamyl alcohol (25:24:1), once with CHCl$_3$/isoamyl alcohol and ethanol precipitated. The DNA was resuspended in water and 5 μg was ligated in a 500 μl reaction according to the manufacturer's instructions (Promega). The ligation mix was transformed into HB101 by electroporation and plated on LB plus 100 μg/ml ampicillin (LB Amp). 500 colonies were picked into individual wells of 96 well microtiter plates containing 50 μl LB Amp and grown overnight at 37° C. The colonies were then replica plated onto a 150 mm petri plate containing LB Amp and grown overnight. Colony lifts were prepared with Hybon N+ (Amersham), and the filters probed. Nine positive colonies were obtained, four of which showed a restriction pattern that did not match that expected for an inverted repeat of T-DNA. Three of the four were identical (pCTG1) and these were then used to probe Southern blots to confirm that they contained plant DNA. The fourth isolate contained a co-cloned fragment as evidenced by the presence of an additional SalI site.

Figure 7A:
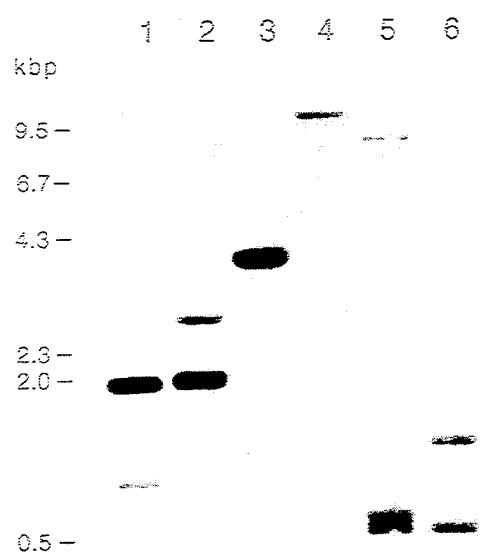
FIGS. 7A-7B exhibits Southern and Northern Analysis of the CTR1 gene.

Southern blot analysis of wild-type and ctr1-5 DNA revealed that the insertional line showed an altered size of restriction fragments hybridizing to the probe indicating that the rescued DNA did indeed flank the site of T-DNA insertion, see FIG. 7A. The flanking plant DNA was used to screen genomic and cDNA libraries. The rescued plant DNA was used to isolate several lambda genomic clones and a detailed physical map of the region was constructed.

One of the genomic clones, λctg24, detected a RFLP between two different Arabidopsis ecotypes and this was used to map the cloned DNA using a population of 83 F8 recombinant inbred lines. The CTR1 gene mapped close to the RFLPs g3715 and λ217, see FIG. 3, the clones also showed complete linkage with the ctr1 mutation (0 recombinants/86 chromosomes) using DNA from a ctr1 F2 mapping population. Hybridization of RFLP probes to several Arabidopsis YAC libraries revealed that CTR1 and λ447 were contained within identical YACs, the smallest of which had an 80 kbp insert (FIG. 3). This analysis showed that the clones mapped very close to the ubq6-12-1 RFLP (1/154 recombinants), and at, or very close to the ctr1 mutation (0/78 recombinants).

Plant DNA was isolated from pCTG1 and used to probe an Arabidopsis genomic library in λEMBL (Clontech) and λDASH (gift of Dr. Nigel Crawford). Restriction maps were made of the clones, two were picked that overlapped (λctg1 and λctg24) and were in opposite orientation and these were used to probe a cDNA library constructed in λZAPII (Stratagene).

Using 5 μg poly (A)+RNA from 3 day old dark-grown, ethylene-treated Arabidopsis seedlings (hypocotyls and cotyledons) as template and oligo d(T) as primer, first strand cDNA synthesis was catalyzed by Moloney Murine Leukemia Virus reverse transcriptase (Pharmacia). Second-strand cDNA was made as described except that DNA ligase was omitted. After the second strand reaction, the ends of the cDNA were made blunt with Klenow fragment and EcoRI/Not I adaptors (Pharmacia) were ligated to each end. The cDNA was purified from unligated adaptors by spun-column chromatography using Sephacryl S-300 and size fractionated on a 1% low melting point mini-gel. Size-selected cDNAs (0.5–1 kb, 1–2 kb, 2–3 kb, 3–6 kb) were removed from the gel using agarase (New England Biolabs), phenol:chloroform extracted and precipitated using 0.3M NaOAc (pH 7)/ethanol. A portion of each cDNA size-fraction (0.1 μg) was co-precipitated with 1 μg of λZAPII (Stratagene) EcoRI-digested, dephosphorylated arms then ligated in a volume of 4 μl overnight. Each ligation mix was packaged in vitro using a Gigapack II Gold packaging extract (Stratagene).

Clones that hybridized to both probes were picked, and all were found to be similar by restriction pattern. Thirty one of these were picked and restriction mapped, seven were sequenced from both ends and two were sequenced completely.

Figure 7B:
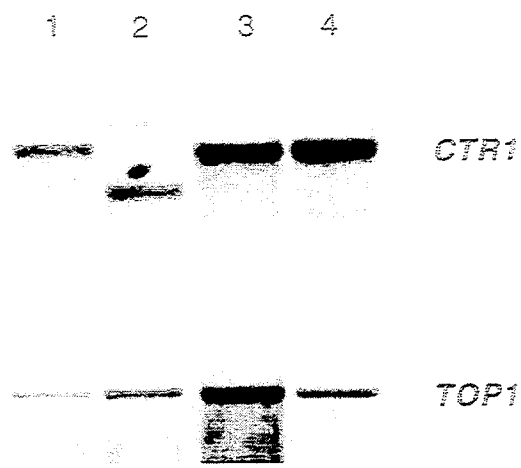

Northern blot analysis using one of the cDNA clones (λctc2-1) as a probe detected a single transcript of 3.2 kb in seedling and adult plants grown in air and ethylene, FIG. 7B. Expression of CTR1 mRNA was disrupted in the T-DNA insertion allele. The T-DNA line, ctr1-5, showed two transcripts, one larger and one smaller than the wild-type transcript, probably due to two different termination signals present in the T-DNA. The presence of two CTR1 homologous transcripts in ctr1-5 may result from termination at, or splicing to, multiple sites within the T-DNA. Alternatively, transcription initiation from a promoter close to the right border of T-DNA insertion may have resulted in expression of CTR1 sequence 3' to the insertion site. The size of the CTR1 transcript seen in the Northern blots indicates that several of the cDNA clones are near full length.

TO prove that the clones did in fact represent the authentic CTR1 gene, the wild-type and several mutant alleles were sequenced. The cDNA and genomic clones were subcloned into pKS (Stratagene) and exonuclease III deletions were performed as described by Sambrook et al., *Molecular Cloning: A Laboratory Manual*, 2nd ed., Cold Spring Harbor Laboratory Press, Cold Spring Harbor, N.Y. (1989). DNA sequencing was done on a Applied Biosystem automated DNA sequencer (model 373A) using dye terminators as recommended by the manufacturer and also using SEQUENASE ™ version 2 as described by the manufacturer (United States Biochemicals). All regions were sequenced on both stands at least one time. Synthetic oligonucleotide primers were made (18-19 bp, at least 50% GC) that would enable the exons to be sequenced. DNA was prepared from the mutant alleles by CsCl purification as described and four sets of primers were used to amplify the CTR1 gene from the mutants using the polymerase chain reaction, PCR. Internal restriction sites in the various PCR products were used to subclone the fragments into pKS and the exons sequenced using the synthetic oligonucleotides. Conditions for PCR were as follows: 35 cycles of 1' at 92° C., 1' at 55° C. and 3' at 72° C. in a Bioscycler (Bios Corp.). Taq DNA polymerase (Promega) was added after the mix was preheated to 92° C. Internal restriction sites in the various PCR products were used to subclone the fragments into pKS (Stratagene) and the exons were sequenced using primers specific for the vector (pKS) as well as gene-specific primers. Any alterations observed in the DNA sequence of the mutant alleles were re-sequenced from at least two additional independent PCR products. In one case (ctr1-4) the sequence in question was also determined from clones isolated directly from a size-selected EcoRI genomic library made in λZAPII as follows. Twenty μg of genomic DNA from ctr1-4 was cleaved to completion with EcoRI, the DNA electrophoresed through a 0.8% agarose gel and the DNA in the 1.0–1.7 kb range isolated using agarase as described by the manufacturer (New England Biolabs). The size-selected DNA was ligated into EcoRI-digested, and phosphatase-treated λZAPII (Stratagene) and the mix was packaged in vitro using Gigapack II as described by the manufacturer (Stratagene). The phage plaques were screened with a radio-labeled probe corresponding to the 1.4 kb restriction fragment which was suspected of harboring the mutation and the positive phage purified. A plasmid containing insert genomic DNA was rescued by superinfection with helper phage (R408) and the insert was sequenced as described above. Any alterations in the mutations were re-sequenced from at least two additional independent PCR products. In two cases (ctr1-1, ctr1-4), the sequence in question was also sequenced from clones isolated directly from a sublibrary made in λZAPI.

All five of the mutant alleles are associated with sequence alterations in this gene, demonstrating conclusively that the clones correspond to the CTR1 gene. The X-ray allele, ctr1-2, SEQUENCE ID NO: 4, was due to a 17 base pair deletion beginning at position 1995 of the genomic sequence of SEQUENCE ID NO: 3 which is predicted to result in a frame shift in the coding region. One of the EMS mutants, ctr1-3, SEQUENCE ID NO: 5 was due to a C→T transition, resulting in a stop codon at position 1927 of the genomic sequence. In the resulting protein product, "arg" is converted to a stop signal. The other two alterations were single codon changes resulting in amino acid substitutions. Specifically, the ctr1-1 mutation set forth in SEQUENCE ID NO: 6 has a "T" to "A" point mutation at nucleotide position 3295 of CTR genomic DNA sequence in SE- QUENCE ID NO: 3 which is predicted to result in a highly conservative substitution (Asp to Glu) at amino acid position 694. The ctr1-1 mutation of SEQUENCE ID NO: 6 was generated by DEB mutagenesis. Another mutation, ctr1-4, generated by EMS mutagenesis was also the result of a point mutation from a "G" to "A" transition at position 3233 that is predicted to result in a "Glu" to "Lys" change at amino acid 596, another invariant residue in all kinase catalytic domains, see SEQUENCE ID NO: 7. ctr1-5 comprises the T-DNA insertion found at position 3041 in intron 7 and 25 base pairs were deleted from the left border of the T-DNA at the junction with plant DNA.

The cDNA for the CTR1 gene is shown in SEQ ID NO: 1. The CTR1 gene spans approximately 6.5 kb of genomic DNA. Comparison of the cDNA and genomic clones revealed that 14 introns interrupt the CTR1 coding region and that the intron/exon boundaries all fit the consensus for splice donor and acceptor sites fairly well. The introns range in size from 77 bp to 357 bp. As determined by screening of the primary cDNA library, the longest intron (#5) is less efficiently spliced in the mRNA population. Nine of the introns are located in the carboxy-half of the gene, resulting in several very small exons; the smallest (exon #7) is only 41 base pairs. The longest open reading frame is 2466 nucleotides and predicts a protein with a molecular mass of approximately 90 kD. There are two closely spaced methionine codons at the beginning of this open reading frame, either of which could be the authentic start codon as they show reasonable correspondence to the consensus site for plant start codons. The 5" untranslated region is 117 bp in the longest cDNA, and most of the cDNA clones end within 50 base pairs of this site. The size of the 3' non-translated region varies in the different cDNAs, the longest being 453 bp. No poly(A) tail was found in any of the cDNA clones although the size of the longest cDNA matches the transcript size observed in northern blots. The upstream genomic sequence has several putative "TATA" boxes that closely match that of the plant consensus sequence. Approximately 10% (3/31) of the cDNA clones were incompletely spliced as judged by analysis of restriction enzyme digestion patterns. These may represent alternatively spliced products, although only a single transcript is detected by Northern blot analysis.

TABLE 2

Mapping of the ctr1 mutation

| Marker[a] | Progeny Type[b] | Total | Recombinants | Distance[c] |
|---|---|---|---|---|
| Morphological | | | | |
| ttg | F3 (cis) | 228 | 49 | 21.5 ± 6 |
| lu | F2 (trans) | 279 | 2 | 8.0 ± 7 |
| tt4 | F2 (cis) | 250 | 27 | 10.8 ± 3.6 |
| RPLP | | | | |
| 447 | F3[d] | 39 | 0 | 0 ± 4.7 |
| ubq 6-12-1 | F3 | 120 | 1 | 0 ± |
| 217 | | 76 | 2 | 0 ± |
| T-DNA | | | | |
| Km[r] | T3 | 1131 | 0 km[s] | 0 ± 5 |
| ctr | T4 from a single wt, | 265 | 1 did not segregate ctr[e] | 0.4 m.u. ± 1.7 |
| km[r] T3 plant | | | | |

[a]Morphological markers were obtained from the Arabidopsis Stock Center. RFLP markers were kindly provided by E. Meyerwitz.
[b]Progeny were form a cross of a ctr1 mutant to the marker (trans), or a cross of a line mutant for both ctr1 and the marker to wild-type (cis).
[c]Distance is shown with a 95% confidence interval.
[d]The crosses for RFLP analysis were to ecotype Niederzenz.
[e]The single non-segregating line still had T-DNA in the intron as judged by Southern analysis.

EXAMPLE 5

CTR1 is a Member of the RAF Family of Serine/Threonine Kinases

The open reading frame of the longest cDNA clone predicted a protein with a molecular weight of 90,000 containing no obvious membrane-spanning regions. A search of the PROSITE directory with the predicted CTR1 amino acid sequence reveals two signature patterns: one for an ATP binding domain IGAGSFGTV (SEQUENCE ID NO: 9) and one specific for serine/threonine protein kinases SEQUENCE ID NO: 8 (IVHRDLKSPNLLV). A search of the Swiss-prot data bank revealed that the carboxyl half of the gene was highly homologous to various protein kinases. Strong homology (>50% aa) to the Raf family of serine/threonine protein kinases was revealed in the carboxy-terminal 300 amino acids. The 11 subdomains common to all known kinases were highly conserved in the CTR1 gene and homology (49% identity in the kinase domain amino acid numbers 450 to 820) was found to the RAF family of serine/threonine kinases. The occurrence of a tyrosine at amino acid position 735 of CTR protein product resulting from nucleic acid of SEQUENCE ID NO: 2 is unique to RAF family members. The threonine at amino acid position 714 is a strong indicator that the protein is a serine/threonine, rather than a tyrosine kinase, though homology was found to the kyk1 and kyk2 genes from dictyostelium, two putative dual specificity kinases. Weak homology to the RAF genes extends an additional 300 residues upstream of the kinase domain including the presence of a serine rich region in both the RAF genes and CTR1. Also, a cystine finger is present in the 5' half of the RAF gene which is thought to bind to lipids. There is a cystine rich region in CTR1 in the appropriate position, but the spacing of the cystine residues is not consistent with known cystine finger motifs.

A FASTA search of current databases reveals significant homology in the carboxy-half (predicted catalytic domain) of the protein with over 300 known or predicted tyrosine and serine/threonine kinases. The highest degree of homology (41% identity in the kinase domain) is found with members of the Raf family of serine/threonine protein kinases. The CTR1 protein contains conserved residues in subdomain VIB, HRDLKSPN (SEQUENCE ID NO: 10), and subdomain VIII, TPEWMAPE (SEQUENCE ID NO: 11), that strongly suggest serine/threonine specificity. Interestingly, the catalytic domain of CTR1 also shows strong sequence similarity to the KYK1 gene from Dictyostelium, a putative dual specificity kinase.

There are several interesting features in the N-terminus of CTR1. The first exon (217 amino acids) is unusually rich in glycine (12.4%) and serine/threonine (19%), which is also true of the B-Raf N-terminus. There is a consensus nucleotide triphosphate binding loop or P-loop, GXXXXGKS/T where X is any residue and the last amino acid is a S or a T (SEQUENCE ID NO: 12, wherein the last amino acid is S and SEQUENCE ID NO: 13, wherein the last amino acid is T), in the N-terminal half of CTR1, starting at residue 154. This motif is thought to be involved in binding ATP or GTP in a number of proteins, including Ras, but is not generally present in protein kinases. There are also several stretches of consecutive glycine residues in the N-terminal half, a repeat cluster known as PEN, GGX, where X is any residue. Similar repeats are present in a diverse group of proteins, including B-Raf although its function is unknown.

All five ctr1 mutations disrupt the putative catalytic domain. The two amino acid substitutions seen in ctr1-1 and ctr1-4 are both in very highly conserved residues in kinases. The ctr1-1 mutation is a highly conservative aspartic acid→glutamic acid change at amino acid position 694, but this residue is invariant in all known kinases. The site of insertion of T-DNA ctr1-5, the stop codon in ctr1-3, and the 17 base pair deletion in the ctr1-2 x-ray allele are predicted to result in truncation of the CTR1 protein with loss of the kinase domain. The two amino acid substitutions seen in ctr1-1 and ctr1-4 are both in very highly conserved kinase residues. The ctr1-1 mutation is a T→A transversion at position 3295 that is predicted to result in a highly conservative substitution (Asp→Glu) at amino acid 694. However, this Asp residue is invariant in all known kinases. The change in ctr 1-4 is a G→A transition at position 3233 that is predicted to result in a Glu→Lys change at amino acid position 596, another invariant residue in all kinase catalytic domains.

EXAMPLE 6

Ethylene Production from Various Arabidopsis Strains

The amount of ethylene produced by wild-type and a number of mutants etiolated seedlings after three days in the dark was tested with a gas chromatograph in accordance with the methods of Guzman et al., supra, incorporated herein by reference. The constitutive mutants that were reversible by inhibitors of ethylene action (the Eto mutants) all significantly over-produce ethylene, ranging from 10 fold more than wild-type to over 200 fold. ctr1 mutant seedlings produced less ethylene than wild-type seedlings. The Ein mutants have been shown to produce more ethylene than wild-type seedlings. These data suggest that ethylene production is negatively regulated in Arabidopsis seedlings.

EXAMPLE 7

Molecular Analysis of Mutants

To determine whether the pEI305 cDNA is expressed and regulated by ethylene in adult plants, Northern blots containing total RNA from ethylene-treated and air-grown wild-type (wt), ctr1 and eto1 plants were hybridized with pEI305. All plants were grown in continuous light and harvested at the onset of bolting. Hormone was applied to a group of plants for 24 hours by placing them in a chamber through which 10 ppm ethylene was passed. pEI305 transcripts are barely detectable in air-grown wild-type plants, and are strongly elevated in hormone-treated plants. Air-treated eto1 adults show an increase level of transcripts relative to air-treated plants, but also show an induction upon ethylene treatment. In air-treated ctr1 adults, pEI305 transcripts are expressed at even higher levels than ethylene-treated wild-type plants, and higher levels still upon ethylene treatment.

EXAMPLE 8

Adult Phenotypes

Etiolated ctr1 seedlings grown in air were indistinguishable from etiolated wild-type seedlings grown in 10 µl C2H4/liter of air FIG. 2. When shifted to light, ctr1 seedlings opened their apical hook and expanded the cotyledons much more slowly than wild-type seedlings (24-36 hours compared to 4-5 hours for wild-type). ctr1 cotyledons were also darker green than their wild-type counterparts. Wild-type seedlings treated with ACC (an ethylene precursor) showed these same phenotypes.

Figure 2C:
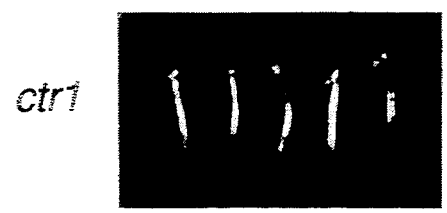
Figure 2D:

The gynoecium of ctr1 elongated significantly earlier relative to the rest of the developing flower, often protruding out of the unopened buds. A fifth allele (ctr1-5), which was generated by T-DNA insertion, showed a more severe phenotype, but this may be due to its genetic background (ctr1-5 is in the Wassilewskija ecotype while ctr1-1 through 1-4 are in the Columbia ecotype). The dramatic adult phenotype of ctr1 suggests that the gene product is involved in the ethylene response pathway of both seedlings and adult plants. The seedling phenotypes of some of these mutants grown in air is shown in FIG. 2C. A second ctr mutant (ctr2) was also identified that complements ctr1.

ctr1 adult mutants showed dramatic morphological differences compared to wild-type plants, see FIG. 2C. The mutant plants have rosette leaves that are epinastic and much smaller and darker green, they bolt approximately 1-2 weeks later, the early flowers are infertile, the root system are much less extensive and the inflorescence is much smaller than in wild-type plants. In ctr1 mutant flowers the stigmatal surface matures significantly earlier during development than in wild-type flowers. These adult phenotypes are seen in all 5 independent alleles of ctr1 and in backcrosses co-segregate 100% with ctr1. The T-DNA allele shows the most severe phenotype, though this may be due to the fact this allele was isolated in a different ecotype (WS verses Columbia for the others). The other alleles are very similar, with the exception of ctr1-3, (SEQUENCE ID NO: 5) which is slightly more infertile. The dramatic adult phenotype of ctr1 mutants suggests that this gene product is involved in the ethylene response pathway of both seedlings and adult plants.

EXAMPLE 9

Growth in Ethylene Phenocopies the ctr1 Phenotype

When adult plants are placed in ethylene, mature leaves chloros and then senesce. However, when wild-type and mutant plants were grown to maturity in the continuous presence of ethylene, they exhibited all the morphological characteristics seen in air-grown ctr1 plants, with the exception that ethylene-treated plants had fewer trichomes than their air-grown counterparts. An ethylene-insensitive mutant, ein2 (Guzman et al., supra) failed to display these morphological alterations. This indicates that Arabidopsis can either adapt to the continuous presence of ethylene, or that newly formed leaves show a different response than fully formed leaves. The adult phenotype of the ctr1 mutant most likely represents a constitutive adult ethylene response. Interestingly, when ctr1 mutant, but not wild-type leaves, are excised and placed in the dark for several days they show significant chlorosis, approaching that seen in wild-type leaves excised and placed in ethylene in the dark.

EXAMPLE 10 ctr1 Mutants Show a Reduction in the Size of Leaf Epidermal Cells

Plants were grown in chambers with air or ethylene as described above for three weeks (until just beginning to bolt). Leaves from the third or fourth true set were excised, placed in 95% ethanol and boiled for 5 minutes. The ethanol was removed, replaced with lactophenol (1:1:1:1 of 85% lactic acid, phenol, glycerol and water) and boiled again for 5 minutes. The leaves were then mounted on slides, examined under Nomarski optics and photographed. Cell sizes and shapes were quantitated by tracing photographs (10 leaves per treatment, approximately 30 cells per photograph) using a tracing tablet and the MacMeasure program, a tracing program which quantitated the reduction in cell size. The shape factor was calculated using the following equation: $SF = 4\pi A/p^2$, where A is the area and p is the perimeter.

To determine the basis for the reduction in size seen in ctr1 mutant and ethylene-treated leaves, the sizes of leaf cells were examined by Nomarski microscopy. Epidermal cells from mutant leaves were significantly reduced in size relative to wild-type cells, and this reduction in cell size could be phenocopied by growth of wild-type plants in the continual presence of lppm ethylene. There also was a higher concentration stomata in the mutant and ethylene-grown plants as compared to air-grown wild-type leaves, which is consistent with the hypothesis that stomata are spaced as a function of cell number, not leaf area. The reduction in the size of the epidermal cells was quantitated using a tracing program (MacMeasure), and the area of the ctr1 epidermal cells was fivefold smaller than cells from air-grown wild-type plants, but indistinguishable from wild-type plants grown in ethylene (Table 3). Thus, the smaller size of ctr1 and ethylene-grown wild-type leaves is due at least in part to a reduction in cell size. The ctr1 mutant and ethylene-treated wild-type leaves were also rounder than wild-type leaves from air-grown plants (Table 3). This is consistent with the hypothesis that ethylene is inhibiting cell elongation, and that the ctr1 mutant leaves never fully elongate, as developing unexpanded leaves are smaller and rounder than fully expanded ones.

TABLE 3

| Measurements of Epidermal Cell Size and Shape | | | |
|---|---|---|---|
| Strain | Growth[a] | Cell Area[b] | Shape Factor[c] |
| Wild-type | Air | 3,209 ± 140 | 0.29 ± 0.008 |
| | Ethylene | 593 ± 24 | 0.69 ± 0.009 |
| ctr1 | Air | 660 ± 23 | 0.63 ± 0.008 |
| | Ethylene | 830 ± 33 | 0.61 ± 0.009 |

[a]Plants were grown continuously in either blowing air or 1 μl $C_2H_4$/liter of air as described in Experimental Procedure.
[b]Mean from ten leaves, approximately 25 cells per leaf expressed in $\mu m^2$ ± the standard error.
[c]The values are from the same sample used for the area measurements, expressed as the mean ± the standard error.

EXAMPLE 11

Complementation Analysis

Complementation and linkage analysis has identified a third distinct recessive ethylene insensitivity locus, designated EIN3. As with ein1 and ein2, ein3 mutants showed insensitivity in all seedling and adult plant ethylene responses. However, unlike ein1 and ein2, genetic analysis revealed that ein3 is epistatic to the constitutive ethylene response mutation. Thus, in the ethylene action pathway of Arabidopsis, the EIN3 gene product acts down-stream of the ETR1/EIN1, EIN2, CTR1 gene products.

Two alleles of the recessive ein3 mutation have been identified. Lack of complementation between ein3-1, an EMS mutant, and ein3-2, a T-DNA insertional mutant indicate that they are allelic. The ein3-2 and ein2-1 mutations complement one another and thus define separate loci. The F2 generation of an ein1-1 (dominant mutation) X ein3-2 cross segregates wild-type progeny demonstrating that ein1 and ein3 are not allelic. However, the observed ratio of 10 mutant: 1 wild-type deviates from the expected 13:3 ratio indicative of two independently assorting alleles. These results suggest that ein1 and ein3 are linked or that there is a genetic interaction between the two loci which leads to altered patterns of inheritance.

Various modifications of the invention in addition to those shown and described herein will be apparent to those skilled in the art from the foregoing description. Such modifications are also intended to fall within the scope of the appended claims.

---

We claim:

1. An isolated nucleic acid sequence comprising the nucleic acid sequence of SEQ ID NO: 1.

2. The isolated nucleic acid sequence comprising the nucleic acid sequence of SEQ ID NO: 6.

3. An isolated nucleic acid sequence comprising the nucleic acid sequence of SEQ ID NO: 4.

4. An isolated nucleic acid sequence comprising the nucleic acid sequence of SEQ ID NO: 5.

5. An isolated nucleic acid sequence comprising the nucleic acid sequence of SEQ ID NO: 7.

6. An isolated nucleic acid sequence of claim 1 having a T-DNA insertion at position 3041.

7. A DNA sequence complementary to an isolated nucleic acid sequence of claim 1.

8. An isolated nucleic acid sequence encoding the amino acid sequence of SEQ ID NO: 2.

9. An isolated nucleic acid sequence comprising the nucleic acid sequence of SEQ ID NO: 3.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 3033 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 118..2583

( x i ) SEQUENCE DESCRIPTION: SEQ ID NO:1:

```
AGAGAAACAA GTGGCTAGCT AGCTCGCCAA ACTTCTTCAA CAATGGCGGT              50

TTCCTAGGGT TTGATGTTTA TATGATCGGG AAACTCTCTC ATCTAGATCG             100

CGATAACTCT CTTTTCC ATG GAA ATG CCC GGT AGA AGA TCT AAT TAC         147
                   Met Glu Met Pro Gly Arg Arg Ser Asn Tyr
                    1               5                   10

ACT TTG CTT AGT CAA TTT TCT GAC GAT CAG GTG TCA GTT TCC GTC        192
Thr Leu Leu Ser Gln Phe Ser Asp Asp Gln Val Ser Val Ser Val
             15                  20                  25

ACC GGA GCT CCT CCG CCT CAC TAT GAT TCC TTG TCG AGC GAA AAC        237
Thr Gly Ala Pro Pro Pro His Tyr Asp Ser Leu Ser Ser Glu Asn
         30                  35                  40

AGG AGC AAC CAT AAC AGC GGG AAC ACC GGG AAA GCT AAG GCG GAG        282
Arg Ser Asn His Asn Ser Gly Asn Thr Gly Lys Ala Lys Ala Glu
         45                  50                  55

AGA GGC GGA TTT GAT TGG GAT CCT AGC GGT GGT GGT GGT GGT GAT        327
Arg Gly Gly Phe Asp Trp Asp Pro Ser Gly Gly Gly Gly Gly Asp
         60                  65                  70

CAT AGG TTG AAT AAT CAA CCG AAT CGG GTT GGG AAT AAT ATG TAT        372
His Arg Leu Asn Asn Gln Pro Asn Arg Val Gly Asn Asn Met Tyr
         75                  80                  85

GCT TCG TCT CTA GGG TTG CAA AGG CAA TCC AGT GGG AGT AGT TTC        417
Ala Ser Ser Leu Gly Leu Gln Arg Gln Ser Ser Gly Ser Ser Phe
         90                  95                  100

GGT GAG AGC TCT TTG TCT GGG GAT TAT TAC ATG CCT ACG CTT TCT        462
Gly Glu Ser Ser Leu Ser Gly Asp Tyr Tyr Met Pro Thr Leu Ser
             105                 110                 115

GCG GCG GCT AAC GAG ATC GAA TCT GTT GGA TTT CCT CAA GAT GAT        507
Ala Ala Ala Asn Glu Ile Glu Ser Val Gly Phe Pro Gln Asp Asp
             120                 125                 130

GGG TTT AGG CTT GGA TTT GGT GGT GGT GGA GGA GAT TTG AGG ATA        552
Gly Phe Arg Leu Gly Phe Gly Gly Gly Gly Gly Asp Leu Arg Ile
             135                 140                 145

CAG ATG GCG GCG GAC TCC GCT GGA GGG TCT TCA TCT GGG AAG AGC        597
Gln Met Ala Ala Asp Ser Ala Gly Gly Ser Ser Ser Gly Lys Ser
             150                 155                 160

TGG GCG CAG CAG ACG GAG GAG AGT TAT CAG CTG CAG CTT GCA TTG        642
Trp Ala Gln Gln Thr Glu Glu Ser Tyr Gln Leu Gln Leu Ala Leu
             165                 170                 175

GCG TTA AGG CTT TCG TCG GAG GCT ACT TGT GCC GAC GAT CCG AAC        687
Ala Leu Arg Leu Ser Ser Glu Ala Thr Cys Ala Asp Asp Pro Asn
             180                 185                 190

TTT CTG GAT CCT GTA CCG GAC GAG TCT GCT TTA CGG ACT TCG CCA        732
Phe Leu Asp Pro Val Pro Asp Glu Ser Ala Leu Arg Thr Ser Pro
             195                 200                 205

AGT TCA GCC GAA ACC GTT TCA CAT CGT TTC TGG GTT AAT GGC TGC        777
Ser Ser Ala Glu Thr Val Ser His Arg Phe Trp Val Asn Gly Cys
             210                 215                 220
```

```
TTA TCG TAC TAT GAT AAA GTT CCT GAT GGG TTT TAT ATG ATG AAT   822
Leu Ser Tyr Tyr Asp Lys Val Pro Asp Gly Phe Tyr Met Met Asn
225                 230                 235

GGT CTG GAT CCC TAT ATT TGG ACC TTA TGC ATC GAC CTG CAT GAA   867
Gly Leu Asp Pro Tyr Ile Trp Thr Leu Cys Ile Asp Leu His Glu
                240                 245                 250

AGT GGT CGC ATC CCT TCA ATT GAA TCA TTA AGA GCT GTT GAT TCT   912
Ser Gly Arg Ile Pro Ser Ile Glu Ser Leu Arg Ala Val Asp Ser
                255                 260                 265

GGT GTT GAT TCT TCG CTT GAA GCG ATC ATA GTT GAT AGG CGT AGT   957
Gly Val Asp Ser Ser Leu Glu Ala Ile Ile Val Asp Arg Arg Ser
                270                 275                 280

GAT CCA GCC TTC AAG GAA CTT CAC AAT AGA GTC CAC GAC ATA TCT  1002
Asp Pro Ala Phe Lys Glu Leu His Asn Arg Val His Asp Ile Ser
                285                 290                 295

TGT AGC TGC ATT ACC ACA AAA GAG GTT GTT GAT CAG CTG GCA AAG  1047
Cys Ser Cys Ile Thr Thr Lys Glu Val Val Asp Gln Leu Ala Lys
                300                 305                 310

CTT ATC TGC AAT CGT ATG GGG GGT CCA GTT ATC ATG GGG GAA GAT  1092
Leu Ile Cys Asn Arg Met Gly Gly Pro Val Ile Met Gly Glu Asp
                315                 320                 325

GAG TTG GTT CCC ATG TGG AAG GAG TGC ATT GAT GGT CTA AAA GAA  1137
Glu Leu Val Pro Met Trp Lys Glu Cys Ile Asp Gly Leu Lys Glu
                330                 335                 340

ATC TTT AAA GTG GTG GTT CCC ATA GGT AGC CTC TCT GTT GGA CTC  1182
Ile Phe Lys Val Val Val Pro Ile Gly Ser Leu Ser Val Gly Leu
                345                 350                 355

TGC AGA CAT CGA GCT TTA CTC TTC AAA GTA CTG GCT GAC ATA ATT  1227
Cys Arg His Arg Ala Leu Leu Phe Lys Val Leu Ala Asp Ile Ile
                360                 365                 370

GAT TTA CCC TGT CGA ATT GCC AAA GGA TGT AAA TAT TGT AAT AGA  1272
Asp Leu Pro Cys Arg Ile Ala Lys Gly Cys Lys Tyr Cys Asn Arg
                375                 380                 385

GAC GAT GCC GCT TCG TGC CTT GTC AGG TTT GGG CTT GAT AGG GAG  1317
Asp Asp Ala Ala Ser Cys Leu Val Arg Phe Gly Leu Asp Arg Glu
                390                 395                 400

TAC CTG GTT GAT TTA GTA GGA AAG CCA GGT CAC TTA TGG GAG CCT  1362
Tyr Leu Val Asp Leu Val Gly Lys Pro Gly His Leu Trp Glu Pro
                405                 410                 415

GAT TCC TTG CTA AAT GGT CCT TCA TCT ATC TCA ATT TCT TCT CCT  1407
Asp Ser Leu Leu Asn Gly Pro Ser Ser Ile Ser Ile Ser Ser Pro
                420                 425                 430

CTG CGG TTT CCA CGA CCA AAG CCA GTT GAA CCC GCA GTC GAT TTT  1452
Leu Arg Phe Pro Arg Pro Lys Pro Val Glu Pro Ala Val Asp Phe
                435                 440                 445

AGG TTA CTA GCC AAA CAA TAT TTC TCC GAT AGC CAG TCT CTT AAT  1497
Arg Leu Leu Ala Lys Gln Tyr Phe Ser Asp Ser Gln Ser Leu Asn
                450                 455                 460

CTT GTT TTC GAT CCT GCA TCA GAT GAT ATG GGA TTC TCA ATG TTT  1542
Leu Val Phe Asp Pro Ala Ser Asp Asp Met Gly Phe Ser Met Phe
                465                 470                 475

CAT AGG CAA TAT GAT AAT CCG GGT GGA GAG AAT GAC GCA TTG GCA  1587
His Arg Gln Tyr Asp Asn Pro Gly Gly Glu Asn Asp Ala Leu Ala
                480                 485                 490

GAA AAT GGT GGT GGG TCT TTG CCA CCC AGT GCT AAT ATG CCT CCA  1632
Glu Asn Gly Gly Gly Ser Leu Pro Pro Ser Ala Asn Met Pro Pro
                495                 500                 505

CAG AAC ATG ATG CGT GCG TCA AAT CAA ATT GAA GCA GCA CCT ATG  1677
Gln Asn Met Met Arg Ala Ser Asn Gln Ile Glu Ala Ala Pro Met
                510                 515                 520

AAT GCC CCA CCA ATC AGT CAG CCA GTT CCA AAC AGG GCA AAT AGG  1722
Asn Ala Pro Pro Ile Ser Gln Pro Val Pro Asn Arg Ala Asn Arg
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     |     | 525 |     |     |     |     | 530 |     |     |     |     | 535 |      |
| GAA | CTT | GGA | CTT | GAT | GGT | GAT | GAT | ATG | GAC | ATC | CCG | TGG | TGT | GAT | 1767 |
| Glu | Leu | Gly | Leu | Asp | Gly | Asp | Asp | Met | Asp | Ile | Pro | Trp | Cys | Asp |      |
|     |     |     |     | 540 |     |     |     |     | 545 |     |     |     |     | 550 |      |
| CTT | AAT | ATA | AAA | GAA | AAG | ATT | GGA | GCA | GGT | TCC | TTT | GGC | ACT | GTC | 1812 |
| Leu | Asn | Ile | Lys | Glu | Lys | Ile | Gly | Ala | Gly | Ser | Phe | Gly | Thr | Val |      |
|     |     |     |     | 555 |     |     |     |     | 560 |     |     |     |     | 565 |      |
| CAC | CGT | GCT | GAG | TGG | CAT | GGC | TCG | GAT | GTT | GCT | GTG | AAA | ATT | CTC | 1857 |
| His | Arg | Ala | Glu | Trp | His | Gly | Ser | Asp | Val | Ala | Val | Lys | Ile | Leu |      |
|     |     |     |     | 570 |     |     |     |     | 575 |     |     |     |     | 580 |      |
| ATG | GAG | CAA | GAC | TTC | CAT | GCT | GAG | CGT | GTT | AAT | GAG | TTC | TTA | AGA | 1902 |
| Met | Glu | Gln | Asp | Phe | His | Ala | Glu | Arg | Val | Asn | Glu | Phe | Leu | Arg |      |
|     |     |     |     | 585 |     |     |     |     | 590 |     |     |     |     | 595 |      |
| GAG | GTT | GCG | ATA | ATG | AAA | CGC | CTT | CGC | CAC | CCT | AAC | ATT | GTT | CTC | 1947 |
| Glu | Val | Ala | Ile | Met | Lys | Arg | Leu | Arg | His | Pro | Asn | Ile | Val | Leu |      |
|     |     |     |     | 600 |     |     |     |     | 605 |     |     |     |     | 610 |      |
| TTC | ATG | GGT | GCG | GTC | ACT | CAA | CCT | CCA | AAT | TTG | TCA | ATA | GTG | ACA | 1992 |
| Phe | Met | Gly | Ala | Val | Thr | Gln | Pro | Pro | Asn | Leu | Ser | Ile | Val | Thr |      |
|     |     |     |     | 615 |     |     |     |     | 620 |     |     |     |     | 625 |      |
| GAA | TAT | TTG | TCA | AGA | GGT | AGT | TTA | TAC | AGA | CTT | TTG | CAT | AAA | AGT | 2037 |
| Glu | Tyr | Leu | Ser | Arg | Gly | Ser | Leu | Tyr | Arg | Leu | Leu | His | Lys | Ser |      |
|     |     |     |     | 630 |     |     |     |     | 635 |     |     |     |     | 640 |      |
| GGA | GCA | AGG | GAG | CAA | TTA | GAT | GAG | AGA | CGT | CGC | CTG | AGT | ATG | GCT | 2082 |
| Gly | Ala | Arg | Glu | Gln | Leu | Asp | Glu | Arg | Arg | Arg | Leu | Ser | Met | Ala |      |
|     |     |     |     | 645 |     |     |     |     | 650 |     |     |     |     | 655 |      |
| TAT | GAT | GTG | GCT | AAG | GGA | ATG | AAT | TAT | CTT | CAC | AAT | CGC | AAT | CCT | 2127 |
| Tyr | Asp | Val | Ala | Lys | Gly | Met | Asn | Tyr | Leu | His | Asn | Arg | Asn | Pro |      |
|     |     |     |     | 660 |     |     |     |     | 665 |     |     |     |     | 670 |      |
| CCA | ATT | GTG | CAT | AGA | GAT | CTA | AAA | TCT | CCA | AAC | TTA | TTG | GTT | GAC | 2172 |
| Pro | Ile | Val | His | Arg | Asp | Leu | Lys | Ser | Pro | Asn | Leu | Leu | Val | Asp |      |
|     |     |     |     | 675 |     |     |     |     | 680 |     |     |     |     | 685 |      |
| AAA | AAA | TAT | ACA | GTC | AAG | GTT | TGT | GAT | TTT | GGT | CTC | TCG | CGA | TTG | 2217 |
| Lys | Lys | Tyr | Thr | Val | Lys | Val | Cys | Asp | Phe | Gly | Leu | Ser | Arg | Leu |      |
|     |     |     |     | 690 |     |     |     |     | 695 |     |     |     |     | 700 |      |
| AAG | GCC | AGC | ACG | TTT | CTT | TCC | TCG | AAG | TCA | GCA | GCT | GGA | ACC | CCC | 2262 |
| Lys | Ala | Ser | Thr | Phe | Leu | Ser | Ser | Lys | Ser | Ala | Ala | Gly | Thr | Pro |      |
|     |     |     |     | 705 |     |     |     |     | 710 |     |     |     |     | 715 |      |
| GAG | TGG | ATG | GCA | CCA | GAA | GTC | CTG | CGA | GAT | GAG | CCG | TCT | AAT | GAA | 2307 |
| Glu | Trp | Met | Ala | Pro | Glu | Val | Leu | Arg | Asp | Glu | Pro | Ser | Asn | Glu |      |
|     |     |     |     | 720 |     |     |     |     | 725 |     |     |     |     | 730 |      |
| AAG | TCA | GAT | GTG | TAC | AGC | TTC | GGG | GTC | ATC | TTG | TGG | GAG | CTT | GCT | 2352 |
| Lys | Ser | Asp | Val | Tyr | Ser | Phe | Gly | Val | Ile | Leu | Trp | Glu | Leu | Ala |      |
|     |     |     |     | 735 |     |     |     |     | 740 |     |     |     |     | 745 |      |
| ACA | TTG | CAA | CAA | CCA | TGG | GGT | AAC | TTA | AAT | CCG | GCT | CAG | GTT | GTA | 2397 |
| Thr | Leu | Gln | Gln | Pro | Trp | Gly | Asn | Leu | Asn | Pro | Ala | Gln | Val | Val |      |
|     |     |     |     | 750 |     |     |     |     | 755 |     |     |     |     | 760 |      |
| GCT | GCG | GTT | GGT | TTC | AAG | TGT | AAA | CGG | CTG | GAG | ATC | CCG | CGT | AAT | 2442 |
| Ala | Ala | Val | Gly | Phe | Lys | Cys | Lys | Arg | Leu | Glu | Ile | Pro | Arg | Asn |      |
|     |     |     |     | 765 |     |     |     |     | 770 |     |     |     |     | 775 |      |
| CTG | AAT | CCT | CAG | GTT | GCA | GCC | ATA | ATC | GAG | GGT | TGT | TGG | ACC | AAT | 2487 |
| Leu | Asn | Pro | Gln | Val | Ala | Ala | Ile | Ile | Glu | Gly | Cys | Trp | Thr | Asn |      |
|     |     |     |     | 780 |     |     |     |     | 785 |     |     |     |     | 790 |      |
| GAG | CCA | TGG | AAG | CGT | CCA | TCA | TTT | GCA | ACT | ATA | ATG | GAC | TTG | CTA | 2532 |
| Glu | Pro | Trp | Lys | Arg | Pro | Ser | Phe | Ala | Thr | Ile | Met | Asp | Leu | Leu |      |
|     |     |     |     | 795 |     |     |     |     | 800 |     |     |     |     | 805 |      |
| AGA | CCA | TTG | ATC | AAA | TCA | GCG | GTT | CCT | CCG | CCC | AAC | CGC | TCG | GAT | 2577 |
| Arg | Pro | Leu | Ile | Lys | Ser | Ala | Val | Pro | Pro | Pro | Asn | Arg | Ser | Asp |      |
|     |     |     |     | 810 |     |     |     |     | 815 |     |     |     |     | 820 |      |

| TTG | TAAAATACCC | CCGGTCCATT | CAAAAGTTGT | TATAATCATG | ATATGCACAT | 2630 |
| --- | --- | --- | --- | --- | --- | --- |
| Leu |     |     |     |     |     |     |

ATACTCTCAG CATTCTTTTG CTGCCCAGGA GGGAGACACT AGTTAAGATA         2680

-continued

```
TAGCTTTAAA GGTACATTCC TCATGAGCTA TCAATCATAT CCTACAGAAT         2730
CCCATGGTTT TTATACATGT ATTATTTTTG CGATCTTTGT CTGCTGTTTT         2780
GTTCCCTTTT TAATGTTGCA GATTGTTAAA ATGTACATGA CTATTGTCAC         2830
AGGGAGGAAA AAAAAATGTA GTAATGGAAA CAATGTGAGG GATATAATCT         2880
ATCTATCTAG TCCCAAGGG  TAAGCAATAT TGTGTTGTTA TGTCTTTGTA         2930
GCAATGCACT GAAAGCTATA TTTAATTACA TTGCTGTACA TTTATACCGC         2980
TAAATTAGTT ACTAAGCGAA GGTAAAAAAG AGCAGCTGGT AAATGCTGTC         3030
AAA                                                            3033
```

( 2 ) INFORMATION FOR SEQ ID NO:2:

( i ) SEQUENCE CHARACTERISTICS:
        ( A ) LENGTH: 821 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Met Pro Gly Arg Arg Ser Asn Tyr Thr Leu Leu Ser Gln Phe
 1               5                  10                  15

Ser Asp Asp Gln Val Ser Val Ser Val Thr Gly Ala Pro Pro Pro His
                20                  25                  30

Tyr Asp Ser Leu Ser Ser Glu Asn Arg Ser Asn His Asn Ser Gly Asn
            35                  40                  45

Thr Gly Lys Ala Lys Ala Glu Arg Gly Gly Phe Asp Trp Asp Pro Ser
        50                  55                  60

Gly Gly Gly Gly Gly Asp His Arg Leu Asn Asn Gln Pro Asn Arg Val
 65                 70                  75                  80

Gly Asn Asn Met Tyr Ala Ser Ser Leu Gly Leu Gln Arg Gln Ser Ser
                85                  90                  95

Gly Ser Ser Phe Gly Glu Ser Ser Leu Ser Gly Asp Tyr Tyr Met Pro
                100                 105                 110

Thr Leu Ser Ala Ala Ala Asn Glu Ile Glu Ser Val Gly Phe Pro Gln
            115                 120                 125

Asp Asp Gly Phe Arg Leu Gly Phe Gly Gly Gly Gly Gly Asp Leu Arg
        130                 135                 140

Ile Gln Met Ala Ala Asp Ser Ala Gly Gly Ser Ser Ser Gly Lys Ser
145                 150                 155                 160

Trp Ala Gln Gln Thr Glu Glu Ser Tyr Gln Leu Gln Leu Ala Leu Ala
                165                 170                 175

Leu Arg Leu Ser Ser Glu Ala Thr Cys Ala Asp Asp Pro Asn Phe Leu
            180                 185                 190

Asp Pro Val Pro Asp Glu Ser Ala Leu Arg Thr Ser Pro Ser Ser Ala
        195                 200                 205

Glu Thr Val Ser His Arg Phe Trp Val Asn Gly Cys Leu Ser Tyr Tyr
    210                 215                 220

Asp Lys Val Pro Asp Gly Phe Tyr Met Met Asn Gly Leu Asp Pro Tyr
225                 230                 235                 240

Ile Trp Thr Leu Cys Ile Asp Leu His Glu Ser Gly Arg Ile Pro Ser
                245                 250                 255

Ile Glu Ser Leu Arg Ala Val Asp Ser Gly Val Asp Ser Ser Leu Glu
            260                 265                 270

Ala Ile Ile Val Asp Arg Arg Ser Asp Pro Ala Phe Lys Glu Leu His
        275                 280                 285
```

| | | | | | | | | | | | | |
|---|---|---|---|---|---|---|---|---|---|---|---|---|
| Asn | Arg 290 | Val | His | Asp | Ile 295 | Ser | Cys | Ser | Cys 300 | Ile | Thr | Lys | Glu | Val |
| Val 305 | Asp | Gln | Leu | Ala | Lys 310 | Leu | Ile | Cys | Asn | Arg 315 | Met | Gly | Gly | Pro | Val 320 |
| Ile | Met | Gly | Glu | Asp 325 | Glu | Leu | Val | Pro | Met 330 | Trp | Lys | Glu | Cys | Ile | Asp 335 |
| Gly | Leu | Lys | Glu 340 | Ile | Phe | Lys | Val | Val 345 | Pro | Ile | Gly | Ser 350 | Leu | Ser |
| Val | Gly | Leu 355 | Cys | Arg | His | Arg | Ala 360 | Leu | Leu | Phe | Lys 365 | Val | Leu | Ala | Asp |
| Ile | Ile | Asp 370 | Leu | Pro | Cys | Arg 375 | Ile | Ala | Lys | Gly | Cys 380 | Lys | Tyr | Cys | Asn |
| Arg 385 | Asp | Asp | Ala | Ala | Ser 390 | Cys | Leu | Val | Arg | Phe 395 | Gly | Leu | Asp | Arg | Glu 400 |
| Tyr | Leu | Val | Asp | Leu 405 | Val | Gly | Lys | Pro | Gly 410 | His | Leu | Trp | Glu | Pro 415 | Asp |
| Ser | Leu | Leu | Asn 420 | Gly | Pro | Ser | Ser | Ile 425 | Ser | Ile | Ser | Ser 430 | Pro | Leu | Arg |
| Phe | Pro | Arg 435 | Pro | Lys | Pro | Val | Glu 440 | Pro | Ala | Val | Asp | Phe 445 | Arg | Leu | Leu |
| Ala | Lys 450 | Gln | Tyr | Phe | Ser | Asp 455 | Ser | Gln | Ser | Leu | Asn 460 | Leu | Val | Phe | Asp |
| Pro 465 | Ala | Ser | Asp | Asp | Met 470 | Gly | Phe | Ser | Met | Phe 475 | His | Arg | Gln | Tyr | Asp 480 |
| Asn | Pro | Gly | Gly | Glu 485 | Asn | Asp | Ala | Leu | Ala 490 | Glu | Asn | Gly | Gly 495 | Ser |
| Leu | Pro | Pro | Ser 500 | Ala | Asn | Met | Pro | Pro 505 | Gln | Asn | Met | Met | Arg 510 | Ala | Ser |
| Asn | Gln | Ile 515 | Glu | Ala | Ala | Pro | Met 520 | Asn | Ala | Pro | Pro | Ile 525 | Ser | Gln | Pro |
| Val | Pro 530 | Asn | Arg | Ala | Asn | Arg 535 | Glu | Leu | Gly | Leu | Asp 540 | Gly | Asp | Asp | Met |
| Asp 545 | Ile | Pro | Trp | Cys | Asp 550 | Leu | Asn | Ile | Lys | Glu 555 | Lys | Ile | Gly | Ala | Gly 560 |
| Ser | Phe | Gly | Thr | Val 565 | His | Arg | Ala | Glu | Trp 570 | His | Gly | Ser | Asp | Val 575 | Ala |
| Val | Lys | Ile | Leu 580 | Met | Glu | Gln | Asp | Phe 585 | His | Ala | Glu | Arg | Val 590 | Asn | Glu |
| Phe | Leu | Arg 595 | Glu | Val | Ala | Ile | Met 600 | Lys | Arg | Leu | Arg | His 605 | Pro | Asn | Ile |
| Val | Leu 610 | Phe | Met | Gly | Ala | Val 615 | Thr | Gln | Pro | Pro | Asn 620 | Leu | Ser | Ile | Val |
| Thr 625 | Glu | Tyr | Leu | Ser | Arg 630 | Gly | Ser | Leu | Tyr | Arg 635 | Leu | Leu | His | Lys | Ser 640 |
| Gly | Ala | Arg | Glu | Gln 645 | Leu | Asp | Glu | Arg | Arg 650 | Arg | Leu | Ser | Met | Ala 655 | Tyr |
| Asp | Val | Ala | Lys 660 | Gly | Met | Asn | Tyr | Leu 665 | His | Asn | Arg | Asn | Pro 670 | Pro | Ile |
| Val | His | Arg 675 | Asp | Leu | Lys | Ser | Pro 680 | Asn | Leu | Leu | Val | Asp 685 | Lys | Lys | Tyr |
| Thr | Val 690 | Lys | Val | Cys | Asp | Phe 695 | Gly | Leu | Ser | Arg | Leu 700 | Lys | Ala | Ser | Thr |
| Phe 705 | Leu | Ser | Ser | Lys | Ser 710 | Ala | Ala | Gly | Thr | Pro 715 | Glu | Trp | Met | Ala | Pro 720 |

|   |   |   |   |   |   |   |   |   |   |   |   |   |
|---|---|---|---|---|---|---|---|---|---|---|---|---|
| Glu | Val | Leu | Arg | Asp<br>725 | Glu | Pro | Ser | Asn | Glu<br>730 | Lys | Ser | Asp | Val | Tyr<br>735 | Ser |
| Phe | Gly | Val | Ile<br>740 | Leu | Trp | Glu | Leu | Ala<br>745 | Thr | Leu | Gln | Gln | Pro<br>750 | Trp | Gly |
| Asn | Leu | Asn<br>755 | Pro | Ala | Gln | Val | Val<br>760 | Ala | Ala | Val | Gly | Phe<br>765 | Lys | Cys | Lys |
| Arg | Leu<br>770 | Glu | Ile | Pro | Arg | Asn<br>775 | Leu | Asn | Pro | Gln | Val<br>780 | Ala | Ala | Ile | Ile |
| Glu<br>785 | Gly | Cys | Trp | Thr | Asn<br>790 | Glu | Pro | Trp | Lys | Arg<br>795 | Pro | Ser | Phe | Ala | Thr<br>800 |
| Ile | Met | Asp | Leu | Leu<br>805 | Arg | Pro | Leu | Ile | Lys<br>810 | Ser | Ala | Val | Pro | Pro<br>815 | Pro |
| Asn | Arg | Ser | Asp<br>820 | Leu |

(2) INFORMATION FOR SEQ ID NO:3:

(i) SEQUENCE CHARACTERISTICS:
        (A) LENGTH: 6312 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| TATAGTCCAT | TCTCTCACTT | TCTATTCTAA | ATATTGTGGA | CGTTATAAAG | 50 |
| GCTTTTTATT | TATTTTATGT | CGAGTTTTTT | AGACTACGTA | GAGCCGAATG | 100 |
| AAAATTTCAT | GTTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |
| TGGTTTAGTA | TTTTACACTG | TGTATGTTCC | TCTTTTAGCT | TTGCGTTTTC | 250 |
| TACTTTCACT | ACGATACTAC | TTTTTATCTT | CCAATTTCAG | TTGCTTATCA | 300 |
| CCAAAATATG | AAATACCAAA | TTAATTGTTT | AAACAGTTTT | ATTAGCGATT | 350 |
| AAATTAGCAC | AAAACATATG | AATAGATATC | ATAGTCGAAT | ACAAAAATTA | 400 |
| GACAAATAAT | AATACACTAA | AAAACAAACT | AAATTGGAGA | ATTGTTTTGA | 450 |
| CAAAAAATAA | AAAAAATGTC | AAAGTTCCAT | AAAAAGGAGG | ACAAAGAGG | 500 |
| AATATAACGA | AATTATCAAC | AGAAACGCAC | CGAGTAAGTT | TATTTCCTAT | 550 |
| GATAACGCAA | AAACAAAAAA | AAAATCCAAT | TCCATTAGAG | AGAGAGAGAG | 600 |
| AGAGAGAGAG | AGAGAGAGAC | TTTTTAGAA | AGTACACAAA | AAAAATGAAA | 650 |
| AACTAGAGAG | AGAAACAAGT | GGCTAGCTAG | CTCGCCAAAC | TTCTTCAACA | 700 |
| ATGGCGGTTT | CCTAGGGTTT | GATGTTTATA | TGATCGGGAA | ACTCTCTCAT | 750 |
| CTAGATCGCG | ATAACTCTCT | TTTCCATGGA | AATGCCCGGT | AGAAGATCTA | 800 |
| ATTACACTTT | GCTTAGTCAA | TTTTCTGACG | ATCAGGTGTC | AGTTTCCGTC | 850 |
| ACCGGAGCTC | CTCCGCCTCA | CTATGATTCC | TTGTCGAGCG | AAAACAGGAG | 900 |
| CAACCATAAC | AGCGGGAACA | CCGGGAAAGC | TAAGGCGGAG | AGAGGCGGAT | 950 |
| TTGATTGGGA | TCCTAGCGGT | GGTGGTGGTG | GTGATCATAG | GTTGAATAAT | 1000 |
| CAACCGAATC | GGGTTGGGAA | TAATATGTAT | GCTTCGTCTC | TAGGGTTGCA | 1050 |
| AAGGCAATCC | AGTGGGAGTA | GTTTCGGTGA | GAGCTCTTTG | TCTGGGGATT | 1100 |
| ATTACATGCC | TACGCTTTCT | GCGGCGGCTA | ACGAGATCGA | ATCTGTTGGA | 1150 |
| TTTCCTCAAG | ATGATGGGTT | TAGGCTTGGA | TTTGGTGGTG | GTGGAGGAGA | 1200 |

| | | | | |
|---|---|---|---|---|
| TTTGAGGATA | CAGATGGCGG | CGGACTCCGC | TGGAGGGTCT | TCATCTGGGA | 1250 |
| AGAGCTGGGC | GCAGCAGACG | GAGGAGAGTT | ATCAGCTGCA | GCTTGCATTG | 1300 |
| GCGTTAAGGC | TTTCGTCGGA | GGCTACTTGT | GCCGACGATC | CGAACTTTCT | 1350 |
| GGATCCTGTA | CCGGACGAGT | CTGCTTACG | GACTTCGCCA | AGTTCAGCCG | 1400 |
| AAACCGTTTC | ACATCGTTTC | TGGGTATTTG | TTCCTGTTAA | GCTTGTTTC | 1450 |
| CCAAAATTAT | TGAATCGTGG | TTATAGAGAT | ATGGTCCTCT | TGTTTCCGAA | 1500 |
| GTTTCAGTTA | GATCTCCTTA | CCAAAAGTCT | ATTAGTAGCA | AATGAGATAT | 1550 |
| GTTGTTTAGA | TACATTGCAG | AGTATGATTG | TTTTGTGTGC | TGCATCAGGT | 1600 |
| TAATGGCTGC | TTATCGTACT | ATGATAAAGT | TCCTGATGGG | TTTTATATGA | 1650 |
| TGAATGGTCT | GGATCCCTAT | ATTTGGACCT | TATGCATCGA | CCTGCATGAA | 1700 |
| AGTGGTCGCA | TCCCTTCAAT | TGAATCATTA | AGAGCTGTTG | ATTCTGGTGT | 1750 |
| TGATTCTTCG | CTTGAAGCGA | TCATAGTTGA | TAGGCGTAGT | GATCCAGCCT | 1800 |
| TCAAGGAACT | TCACAATAGA | GTCCACGACA | TATCTTGTAG | CTGCATTACC | 1850 |
| ACAAAGAGG | TTGTTGATCA | GCTGGCAAAG | CTTATCTGCA | ATCGTATGGG | 1900 |
| GTTTGTACTC | ATACAATCCT | TACTATCCCT | TTGAACTTAT | ATTTTTATAT | 1950 |
| CTTCCTGTGA | TTTCTCACAT | TGTACTCGTT | AATTCTTGCT | TCCCCAGGGG | 2000 |
| TCCAGTTATC | ATGGGGAAG | ATGAGTTGGT | TCCCATGTGG | AAGGAGTGCA | 2050 |
| TTGATGGTCT | AAAAGAAATC | TTTAAAGTGG | TGGTTCCCAT | AGGTAGCCTC | 2100 |
| TCTGTTGGAC | TCTGCAGACA | TCGAGCTTTA | CTCTTCAAAG | TGAGATCCCA | 2150 |
| ACTTTGATGC | TATCCCCATG | ACATTTAAGA | CATCTTGTGA | AATGATCATA | 2200 |
| TAAATTATTG | TGCTTCATCC | ATTTGTTTTT | ATTGGAATAC | ATATGAAGAA | 2250 |
| CGTTGAATGT | GAAAAGTGGT | GTTATTGATT | AGAAAAAAT | AGGTTACTGA | 2300 |
| TAGTTGAATG | TTCCAAAGAA | AAAAGTATT | TTATATCTTC | TATTTGGTGC | 2350 |
| ATGCAGGTAC | TGGCTGACAT | AATTGATTTA | CCCTGTCGAA | TTGCCAAAGG | 2400 |
| ATGTAAATAT | TGTAATAGAG | ACGATGCCGC | TTCGTGCCTT | GTCAGGTTTG | 2450 |
| GGCTTGATAG | GTATGATACA | AGTGATTGCG | AAAGAGCCTT | TATTTTCCTA | 2500 |
| TTTTCTTTGC | TTTTTGTTTC | TGGAAAAACA | ATTATAGCTC | CAAATGTTTC | 2550 |
| GCAGAATATT | AGGTTGATGA | CGTGGAAAAT | TTGTTTTGGT | TTCAGGGAGT | 2600 |
| ACCTGGTTGA | TTTAGTAGGA | AAGCCAGGTC | ACTTATGGGA | GCCTGATTCC | 2650 |
| TTGCTAAATG | GTCCTTCATC | TATCTCAATT | TCTTCTCCTC | TGCGGTTTCC | 2700 |
| ACGACCAAAG | CCAGTTGAAC | CCGCAGTCGA | TTTTAGGTTA | CTAGCCAAAC | 2750 |
| AATATTTCTC | CGATAGCCAG | TCTCTTAATC | TTGTTTTCGA | TCCTGCATCA | 2800 |
| GGTATTCCCA | TACAAAAAC | CTAAATAATA | TGTTAACTTT | TTGCATGCTG | 2850 |
| CTTACATCTC | GTTTTGTATT | TCCCCTAAAA | GAGTAATCTC | CTATCATTTA | 2900 |
| GGGTATTTCT | TGATCATGTC | TCAGTATCTG | AAGTGTTAGT | AGTCTTAGAA | 2950 |
| TGATTCTATT | GTTTGTTTTC | TTGTCTCTTT | TCACTTTAGT | TGTTTTGGC | 3000 |
| TGTTGATGTG | TATGTTTGTT | GGTGGGTTCT | TTGCCTAATG | ATATTTAAGG | 3050 |
| TTAAACTTGT | TAGTCTGCTG | TTCAAGCTTA | TGAATTCTAG | TGCATTTATG | 3100 |
| TGCAAGACTT | GTCTTCTGGA | CTCTAATTTC | TTATATCTGC | TTGTTTGAAT | 3150 |
| GGTTGTAGAT | GATATGGGAT | TCTCAATGTT | TCATAGGCAA | TATGATAATC | 3200 |
| CGGGTGGAGA | GAATGACGCA | TTGGCAGAAA | ATGGTGGTGG | GTCTTTGCCA | 3250 |

| | | | | |
|---|---|---|---|---|
| CCCAGTGCTA | ATATGCCTCC | ACAGAACATG | ATGCGTGCGT | CAAATCAAAT | 3300 |
| TGAAGCAGCA | CCTATGAATG | CCCCACCAAT | CAGTCAGCCA | GTTCCAAACA | 3350 |
| GGGCAAATAG | GGAACTTGGA | CTTGATGGTG | ATGATATGGA | CATCCCGTGG | 3400 |
| TGTGATCTTA | ATATAAAGA | AAAGATTGGA | GCAGGTAATA | ATTTTACGGA | 3450 |
| AAAATTAATG | ATTCGGTCTA | AAAATGCAAA | GAAATATGAA | ATTCTTGAGG | 3500 |
| AAGTGGTTTT | GCTTGGACT | CTGTTCTCGA | ACAAATAAG | GAAAAGTGC | 3550 |
| CACCCATTTT | GAGATTACAT | TCTTCTCTGT | TGCCTTTAAT | TCTTCCACTC | 3600 |
| TAATTTGAGC | GACTGCTCTT | TCAGGTTCCT | TTGGCACTGT | CCACCGTGCT | 3650 |
| GAGTGGCATG | GCTCGGTAAG | AACTTTTTTG | TCAGAATTTA | CGCAGCTGAA | 3700 |
| TTTTTTTTCG | CTCTAAAAAT | TTGGTTGTGA | CTTTTGGATC | TGCTTGGTAT | 3750 |
| TATAAAAGGC | AAAGTTATTG | TATATGTGAC | TCTCCGTTCT | GTCAGAAATT | 3800 |
| AAACACGGAC | AAAAGGTGTC | CCATTTTAGA | TGTATATGTG | TCTTTATATC | 3850 |
| ATAAATTTGT | CTTCCTGTTT | GAATTTTACA | ATTCTATCAC | TAGAAGAATT | 3900 |
| CTAATTTTGA | TTATTGCAGT | AATATTCTCT | ATCAATTTCA | GGATGTTGCT | 3950 |
| GTGAAAATTC | TCATGGAGCA | AGACTTCCAT | GCTGAGCGTG | TTAATGAGTT | 4000 |
| CTTAAGAGAG | GTGCACAAAT | AAAATTTTCT | CTTGATTTTG | GTAATGAACT | 4050 |
| TGTTGTATTA | ATGTCTCCAA | TGATCTTGAT | TCGCTGTCAG | GTTGCGATAA | 4100 |
| TGAAACGCCT | TCGCCACCCT | AACATTGTTC | TCTTCATGGG | TGCGGTCACT | 4150 |
| CAACCTCCAA | ATTTGTCAAT | AGTGACAGAA | TATTTGTCAA | GGTACAATTA | 4200 |
| CTTGGATTTG | GAAGGTTTGA | TGTACTGAGT | GTAGAATTTT | GGCCTATAAT | 4250 |
| GACTCTAATA | CCATGATTTC | TTTCAAACAG | AGGTAGTTTA | TACAGACTTT | 4300 |
| TGCATAAAAG | TGGAGCAAGG | GAGCAATTAG | ATGAGAGACG | TCGCCTGAGT | 4350 |
| ATGGCTTATG | ATGTGGTATG | TTTAACTCCT | TATGTTACAT | GTATGGGTGA | 4400 |
| TTACTTCCTG | ATCTTGGTGT | TTCTTCACAT | GGAACTTTCT | TTCCAATTCT | 4450 |
| CTGTCACAGG | CTAAGGGAAT | GAATTATCTT | CACAATCGCA | ATCCTCCAAT | 4500 |
| TGTGCATAGA | GATCTAAAAT | CTCCAAACTT | ATTGGTTGAC | AAAAAATATA | 4550 |
| CAGTCAAGGT | TTGAATCTAA | ATTAGAAATT | GTTGTGTCCA | ATGTTTTGAT | 4600 |
| TTTGATATTT | TATTCCTCTT | GTGAGACAAG | CTTATATATA | AATTATGATT | 4650 |
| TTTAATTCTA | AATTGGTTTG | GAGACATTAC | AAAAAGGCGT | TAATCTGCTG | 4700 |
| AAACTTAAAA | GATACAGCAG | CCTCAAGCTG | TCGTCTTAAA | AACAATCAGA | 4750 |
| ACATTATTAT | TCTAACTCCT | CAATTTGTCT | TGAAATTTCA | GGTTTGTGAT | 4800 |
| TTTGGTCTCT | CGCGATTGAA | GGCCAGCACG | TTTCTTTCCT | CGAAGTCAGC | 4850 |
| AGCTGGAACC | GTAAGTTCAG | TTTGTTGAA | ACTAAAACAC | GCTGAACAAC | 4900 |
| GTAACTTTCT | TCTAGGTCCT | ATTTCCAATG | GAAGCTAAAT | AATTACTGAC | 4950 |
| TTTGATATAT | CAGCCCGAGT | GGATGGCACC | AGAAGTCCTG | CGAGATGAGC | 5000 |
| CGTCTAATGA | AAAGTCAGAT | GTGTACAGCT | TCGGGGTCAT | CTTGTGGGAG | 5050 |
| CTTGCTACAT | TGCAACAACC | ATGGGGTAAC | TTAAATCCGG | CTCAGGTACT | 5100 |
| TCCCACTCTA | AACATCCCAA | ATAATAATGA | TATTATTTTG | CATTTGGAAG | 5150 |
| TCCCTCACTC | TACATTTCAT | AACATGCTAT | ATATGATCAT | CCAACAAAT | 5200 |
| GTTCCATAGG | TTGTAGCTGC | GGTTGGTTTC | AAGTGTAAAC | GGCTGGAGAT | 5250 |
| CCCGCGTAAT | CTGAATCCTC | AGGTTGCAGC | CATAATCGAG | GGTTGTTGGA | 5300 |

| | | | | | |
|---|---|---|---|---|---|
| CCAAGTACGT | TAAGATTTTC | TATCTCTTTT | TTGAATTCTT | CTTGAATAGA | 5350 |
| CTTCATGTTT | ATGTATGTGT | TTCATTACCA | GTGAGCCATG | GAAGCGTCCA | 5400 |
| TCATTTGCAA | CTATAATGGA | CTTGCTAAGA | CCATTGATCA | AATCAGCGGT | 5450 |
| TCCTCCGCCC | AACCGCTCGG | ATTTGTAAAA | TACCCCGGT | CCATTCAAAA | 5500 |
| GTTGTTATAA | TCATGATATG | CACATATACT | CTCAGCATTC | TTTTGCTGCC | 5550 |
| CAGGAGGGAG | ACACTAGTTA | AGATATAGCT | TTAAAGGTAC | ATTCCTCATG | 5600 |
| AGCTATCAAT | CATATCCTAC | AGAATCCCAT | GGTTTTTATA | CATGTATTAT | 5650 |
| TTTTGCGATC | TTTGTCTGCT | GTTTTGTTCC | CTTTTAATG | TTGCAGATTG | 5700 |
| TTAAAATGTA | CATGACTATT | GTCACAGGGA | GGAAAAAAA | ATGTAGTAAT | 5750 |
| GGAAACAATG | TGAGGGATAT | AATCTATCTA | TCTAGTCCCA | AAGGGTAAGC | 5800 |
| AATATTGTGT | TGTTATGTCT | TTGTAGCAAT | GCACTGAAAG | CTATATTTAA | 5850 |
| TTACATTGCT | GTACATTTAT | ACCGCTAAAT | TAGTTACTAA | GCGAAGGTAA | 5900 |
| AAAAGAGCAG | CTGGTAAATG | CTGTCAAAGG | GTTTTGCAAA | CTCAATATGA | 5950 |
| TTCATTGGAT | TTACATTTGT | TCACTGTGCG | ATTAGTCTGG | ACTATAAACC | 6000 |
| AACAGAAATG | AAATAAGACT | GTAACTTTCG | GAGACTCTAA | TACAGATGAA | 6050 |
| TATAATCCCA | AATCGTTAAA | AACGCATTGG | GACTGAAAAT | ATCTAGATAC | 6100 |
| ATAGTCAACT | ATTTTTGCCT | TCGCGTCTAA | GTAAGTTCCC | ACACTTGAAA | 6150 |
| ACGACTTTAC | CTGTCTTCCG | AATTAATCGT | TTGATGGATC | GGTAACCAAT | 6200 |
| AGGATTGCGT | AAATCAAAAT | TATACAATAT | TAAATTCTGA | AAAAGGAAAC | 6250 |
| ACGAAAAGCG | AATCAGTGAT | TTGTGAGGGC | CCAGTTCCAA | ATTAGAAAGC | 6300 |
| TGACCTGGCA | AA | | | | 6312 |

( 2 ) INFORMATION FOR SEQ ID NO:4:

( i ) SEQUENCE CHARACTERISTICS:
        ( A ) LENGTH: 6295 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| TATAGTCCAT | TCTCTCACTT | TCTATTCTAA | ATATTGTGGA | CGTTATAAAG | 50 |
| GCTTTTTATT | TATTTTATGT | CGAGTTTTTT | AGACTACGTA | GAGCCGAATG | 100 |
| AAAATTTCAT | GTTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |
| TGGTTTAGTA | TTTTACACTG | TGTATGTTCC | TCTTTTAGCT | TTGCGTTTTC | 250 |
| TACTTTCACT | ACGATACTAC | TTTTTATCTT | CCAATTTCAG | TTGCTTATCA | 300 |
| CCAAAATATG | AAATACCAAA | TTAATTGTTT | AAACAGTTTT | ATTAGCGATT | 350 |
| AAATTAGCAC | AAAACATATG | AATAGATATC | ATAGTCGAAT | ACAAAATTA | 400 |
| GACAAATAAT | AATACACTAA | AAAACAAACT | AAATTGGAGA | ATTGTTTTGA | 450 |
| CAAAAAATAA | AAAAAATGTC | AAAGTTCCAT | AAAAAGGAGG | ACAAAGAGG | 500 |
| AATATAACGA | AATTATCAAC | AGAAACGCAC | CGAGTAAGTT | TATTTCCTAT | 550 |
| GATAACGCAA | AAACAAAAAA | AAAATCCAAT | TCCATTAGAG | AGAGAGAGAG | 600 |
| AGAGAGAGAG | AGAGAGAGAC | TTTTTAGAA | AGTACACAAA | AAAATGAAA | 650 |
| AACTAGAGAG | AGAAACAAGT | GGCTAGCTAG | CTCGCCAAAC | TTCTTCAACA | 700 |

```
ATGGCGGTTT CCTAGGGTTT GATGTTTATA TGATCGGGAA ACTCTCTCAT    750
CTAGATCGCG ATAACTCTCT TTTCCATGGA AATGCCCGGT AGAAGATCTA    800
ATTACACTTT GCTTAGTCAA TTTTCTGACG ATCAGGTGTC AGTTTCCGTC    850
ACCGGAGCTC CTCCGCCTCA CTATGATTCC TTGTCGAGCG AAAACAGGAG    900
CAACCATAAC AGCGGGAACA CCGGGAAAGC TAAGGCGGAG AGAGGCGGAT    950
TTGATTGGGA TCCTAGCGGT GGTGGTGGTG GTGATCATAG GTTGAATAAT   1000
CAACCGAATC GGGTTGGGAA TAATATGTAT GCTTCGTCTC TAGGGTTGCA   1050
AAGGCAATCC AGTGGGAGTA GTTTCGGTGA GAGCTCTTTG TCTGGGGATT   1100
ATTACATGCC TACGCTTTCT GCGGCGGCTA ACGAGATCGA ATCTGTTGGA   1150
TTTCCTCAAG ATGATGGGTT TAGGCTTGGA TTTGGTGGTG GTGGAGGAGA   1200
TTTGAGGATA CAGATGGCGG CGGACTCCGC TGGAGGGTCT TCATCTGGGA   1250
AGAGCTGGGC GCAGCAGACG GAGGAGAGTT ATCAGCTGCA GCTTGCATTG   1300
GCGTTAAGGC TTTCGTCGGA GGCTACTTGT GCCGACGATC CGAACTTTCT   1350
GGATCCTGTA CCGGACGAGT CTGCTTTACG GACTTCGCCA AGTTCAGCCG   1400
AAACCGTTTC ACATCGTTTC TGGGTATTTG TTCCTGTTAA GCTTTGTTTC   1450
CCAAAATTAT TGAATCGTGG TTATAGAGAT ATGGTCCTCT TGTTTCCGAA   1500
GTTTCAGTTA GATCTCCTTA CCAAAAGTCT ATTAGTAGCA AATGAGATAT   1550
GTTGTTTAGA TACATTGCAG AGTATGATTG TTTTGTGTGC TGCATCAGGT   1600
TAATGGCTGC TTATCGTACT ATGATAAAGT TCCTGATGGG TTTTATATGA   1650
TGAATGGTCT GGATCCCTAT ATTTGGACCT TATGCATCGA CCTGCATGAA   1700
AGTGGTCGCA TCCCTTCAAT TGAATCATTA AGAGCTGTTG ATTCTGGTGT   1750
TGATTCTTCG CTTGAAGCGA TCATAGTTGA TAGGCGTAGT GATCCAGCCT   1800
TCAAGGAACT TCACAATAGA GTCCACGACA TATCTTGTAG CTGCATTACC   1850
ACAAAGAGG TTGTTGATCA GCTGGCAAAG CTTATCTGCA ATCGTATGGG   1900
GTTTGTACTC ATACAATCCT TACTATCCCT TTGAACTTAT ATTTTATAT   1950
CTTCCTGTGA TTTCTCACAT TGTACTCGTT AATTCTTGCT TCCCCAGGGG   2000
TCCAGTTATC ATGGGGGAAG ATGAGTTGGT TCCCATGTGG AAGGAGTGCA   2050
TTGATGGTCT AAAAGAAATC TTTAAAGTGG TGGTTCCCAT AGGTAGCCTC   2100
TCTGTTGGAC TCTGCAGACA TCGAGCTTTA CTCTTCAAAG TGAGATCCCA   2150
ACTTTGATGC TATCCCCATG ACATTTAAGA CATCTTGTGA AATGATCATA   2200
TAAATTATTG TGCTTCATCC ATTTGTTTTT ATTGGAATAC ATATGAAGAA   2250
CGTTGAATGT GAAAAGTGGT GTTATTGATT AGAAAAAAAT AGGTTACTGA   2300
TAGTTGAATG TTCCAAAGAA AAAAAGTATT TTATATCTTC TATTTGGTGC   2350
ATGCAGGTAC TGGCTGACAT AATTGATTTA CCCTGTCGAA TTGCCAAAGG   2400
ATGTAAATAT TGTAATAGAG ACGATGCCGC TTCGTGCCTT GTCAGGTTTG   2450
GGCTTGATAG GTATGATACA AGTGATTGCG AAAGAGCCTT TATTTCCTA    2500
TTTTCTTTGC TTTTTGTTTC TGGAAAAACA ATTATAGCTC CAAATGTTTC   2550
GCAGAATATT AGGTTGATGA CGTGGAAAAT TTGTTTTGGT TTCAGGGAGT   2600
ACCTGGTTGA TTTAGTAGGA AAGCCAGGTC ACTTATGGGA GCCTGATTCC   2650
TTGCTAAATG GTCCTTCATC TATCTCAATT TCTTCTCCTC TGCGGTTTCC   2700
ACGACCAAAG CCAGTTGAAC CCGCAGTCGA TTTTAGGTTA CTAGCCAAAC   2750
```

| | | | | | |
|---|---|---|---|---|---|
| AATATTTCTC | CGATAGCCAT | CGATCCTGCA | TCAGGTATTC | CCATACAAAA | 2800 |
| AACCTAAATA | ATATGTTAAC | TTTTTGCATG | CTGCTTACAT | CTCGTTTTGT | 2850 |
| ATTTCCCCTA | AAAGAGTAAT | CTCCTATCAT | TTAGGGTATT | TCTTGATCAT | 2900 |
| GTCTCAGTAT | CTGAAGTGTT | AGTAGTCTTA | GAATGATTCT | ATTGTTTGTT | 2950 |
| TTCTTGTCTC | TTTTCACTTT | AGTTGTTTTT | GGCTGTTGAT | GTGTATGTTT | 3000 |
| GTTGGTGGGT | TCTTTGCCTA | ATGATATTTA | AGGTAAACT | TGTTAGTCTG | 3050 |
| CTGTTCAAGC | TTATGAATTC | TAGTGCATTT | ATGTGCAAGA | CTTGTCTTCT | 3100 |
| GGACTCTAAT | TTCTTATATC | TGCTTGTTTG | AATGGTTGTA | GATGATATGG | 3150 |
| GATTCTCAAT | GTTTCATAGG | CAATATGATA | ATCCGGGTGG | AGAGAATGAC | 3200 |
| GCATTGGCAG | AAAATGGTGG | TGGGTCTTTG | CCACCCAGTG | CTAATATGCC | 3250 |
| TCCACAGAAC | ATGATGCGTG | CGTCAAATCA | AATTGAAGCA | GCACCTATGA | 3300 |
| ATGCCCCACC | AATCAGTCAG | CCAGTTCCAA | ACAGGGCAAA | TAGGGAACTT | 3350 |
| GGACTTGATG | GTGATGATAT | GGACATCCCG | TGGTGTGATC | TTAATATAAA | 3400 |
| AGAAAAGATT | GGAGCAGGTA | ATAATTTTAC | GGAAAAATTA | ATGATTCGGT | 3450 |
| CTAAAAATGC | AAAGAATAT | GAAATTCTTG | AGGAAGTGGT | TTTGCTTTGG | 3500 |
| ACTCTGTTCT | CGAACAAAAT | AAGGAAAAAG | TGCCACCCAT | TTTGAGATTA | 3550 |
| CATTCTTCTC | TGTTGCCTTT | AATTCTTCCA | CTCTAATTTG | AGCGACTGCT | 3600 |
| CTTTCAGGTT | CCTTTGGCAC | TGTCCACCGT | GCTGAGTGGC | ATGGCTCGGT | 3650 |
| AAGAACTTTT | TTGTCAGAAT | TTACGCAGCT | GAATTTTTTT | TCGCTCTAAA | 3700 |
| AATTTGGTTG | TGACTTTTGG | ATCTGCTTGG | TATTATAAAA | GGCAAAGTTA | 3750 |
| TTGTATATGT | GACTCTCCGT | TCTGTCAGAA | ATTAAACACG | GACAAAAGGT | 3800 |
| GTCCCATTTT | AGATGTATAT | GTGTCTTTAT | ATCATAAATT | TGTCTTCCTG | 3850 |
| TTTGAATTTT | ACAATTCTAT | CACTAGAAGA | ATTCTAATTT | TGATTATTGC | 3900 |
| AGTAATATTC | TCTATCAATT | TCAGGATGTT | GCTGTGAAAA | TTCTCATGGA | 3950 |
| GCAAGACTTC | CATGCTGAGC | GTGTTAATGA | GTTCTTAAGA | GAGGTGCACA | 4000 |
| AATAAAATTT | TCTCTTGATT | TTGGTAATGA | ACTTGTTGTA | TTAATGTCTC | 4050 |
| CAATGATCTT | GATTCGCTGT | CAGGTTGCGA | TAATGAAACG | CCTTCGCCAC | 4100 |
| CCTAACATTG | TTCTCTTCAT | GGGTGCGGTC | ACTCAACCTC | CAAATTTGTC | 4150 |
| AATAGTGACA | GAATATTTGT | CAAGGTACAA | TTACTTGGAT | TTGGAAGGTT | 4200 |
| TGATGTACTG | AGTGTAGAAT | TTTGGCCTAT | AATGACTCTA | ATACCATGAT | 4250 |
| TTCTTTCAAA | CAGAGGTAGT | TTATACAGAC | TTTTGCATAA | AAGTGGAGCA | 4300 |
| AGGGAGCAAT | TAGATGAGAG | ACGTCGCCTG | AGTATGGCTT | ATGATGTGGT | 4350 |
| ATGTTAACT | CCTTATGTTA | CATGTATGGG | TGATTACTTC | CTGATCTTGG | 4400 |
| TGTTTCTTCA | CATGGAACTT | TCTTTCCAAT | TCTCTGTCAC | AGGCTAAGGG | 4450 |
| AATGAATTAT | CTTCACAATC | GCAATCCTCC | AATTGTGCAT | AGAGATCTAA | 4500 |
| AATCTCCAAA | CTTATTGGTT | GACAAAAAAT | ATACAGTCAA | GGTTTGAATC | 4550 |
| TAAATTAGAA | ATTGTTGTGT | CCAATGTTTT | GATTTTGATA | TTTTATTCCT | 4600 |
| CTTGTGAGAC | AAGCTTATAT | ATAAATTATG | ATTTTAATT | CTAAATTGGT | 4650 |
| TTGGAGACAT | TACAAAAAGG | CGTTAATCTG | CTGAAACTTA | AAAGATACAG | 4700 |
| CAGCCTCAAG | CTGTCGTCTT | AAAAACAATC | AGAACATTAT | TATTCTAACT | 4750 |
| CCTCAATTTG | TCTTGAAATT | TCAGGTTTGT | GATTTTGGTC | TCTCGCGATT | 4800 |

| | | | | | |
|---|---|---|---|---|---|
| GAAGGCCAGC | ACGTTTCTTT | CCTCGAAGTC | AGCAGCTGGA | ACCGTAAGTT | 4850 |
| CAGTTTGTTT | GAAACTAAAA | CACGCTGAAC | AACGTAACTT | TCTTCTAGGT | 4900 |
| CCTATTTCCA | ATGGAAGCTA | AATAATTACT | GACTTTGATA | TATCAGCCCG | 4950 |
| AGTGGATGGC | ACCAGAAGTC | CTGCGAGATG | AGCCGTCTAA | TGAAAAGTCA | 5000 |
| GATGTGTACA | GCTTCGGGGT | CATCTTGTGG | GAGCTTGCTA | CATTGCAACA | 5050 |
| ACCATGGGGT | AACTTAAATC | CGGCTCAGGT | ACTTCCCACT | CTAAACATCC | 5100 |
| CAAATAATAA | TGATATTATT | TTGCATTTGG | AAGTCCCTCA | CTCTACATTT | 5150 |
| CATAACATGC | TATATATGAT | CATCCAACAA | AATGTTCCAT | AGGTTGTAGC | 5200 |
| TGCGGTTGGT | TTCAAGTGTA | AACGGCTGGA | GATCCCGCGT | AATCTGAATC | 5250 |
| CTCAGGTTGC | AGCCATAATC | GAGGGTTGTT | GGACCAAGTA | CGTTAAGATT | 5300 |
| TTCTATCTCT | TTTTTGAATT | CTTCTTGAAT | AGACTTCATG | TTTATGTATG | 5350 |
| TGTTTCATTA | CCAGTGAGCC | ATGGAAGCGT | CCATCATTTG | CAACTATAAT | 5400 |
| GGACTTGCTA | AGACCATTGA | TCAAATCAGC | GGTTCCTCCG | CCCAACCGCT | 5450 |
| CGGATTTGTA | AAATACCCCC | GGTCCATTCA | AAAGTTGTTA | TAATCATGAT | 5500 |
| ATGCACATAT | ACTCTCAGCA | TTCTTTTGCT | GCCCAGGAGG | GAGACACTAG | 5550 |
| TTAAGATATA | GCTTAAAGG | TACATTCCTC | ATGAGCTATC | AATCATATCC | 5600 |
| TACAGAATCC | CATGGTTTTT | ATACATGTAT | TATTTTTGCG | ATCTTTGTCT | 5650 |
| GCTGTTTTGT | TCCCTTTTTA | ATGTTGCAGA | TTGTTAAAAT | GTACATGACT | 5700 |
| ATTGTCACAG | GGAGGAAAAA | AAAATGTAGT | AATGGAAACA | ATGTGAGGGA | 5750 |
| TATAATCTAT | CTATCTAGTC | CCAAAGGGTA | AGCAATATTG | TGTTGTTATG | 5800 |
| TCTTTGTAGC | AATGCACTGA | AAGCTATATT | TAATTACATT | GCTGTACATT | 5850 |
| TATACCGCTA | AATTAGTTAC | TAAGCGAAGG | TAAAAAGAG | CAGCTGGTAA | 5900 |
| ATGCTGTCAA | AGGGTTTTGC | AAACTCAATA | TGATTCATTG | GATTTACATT | 5950 |
| TGTTCACTGT | GCGATTAGTC | TGGACTATAA | ACCAACAGAA | ATGAAATAAG | 6000 |
| ACTGTAACTT | TCGGAGACTC | TAATACAGAT | GAATATAATC | CCAAATCGTT | 6050 |
| AAAAACGCAT | TGGGACTGAA | AATATCTAGA | TACATAGTCA | ACTATTTTTG | 6100 |
| CCTTCGCGTC | TAAGTAAGTT | CCCACACTTG | AAAACGACTT | TACCTGTCTT | 6150 |
| CCGAATTAAT | CGTTGATGG | ATCGGTAACC | AATAGGATTG | CGTAAATCAA | 6200 |
| AATTATACAA | TATTAAATTC | TGAAAAGGA | AACACGAAAA | GCGAATCAGT | 6250 |
| GATTTGTGAG | GGCCCAGTTC | CAAATTAGAA | AGCTGACCTG | GCAAA | 6295 |

( 2 ) INFORMATION FOR SEQ ID NO:5:

( i ) SEQUENCE CHARACTERISTICS:
        ( A ) LENGTH: 6312 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| TATAGTCCAT | TCTCTCACTT | TCTATTCTAA | ATATTGTGGA | CGTTATAAAG | 50 |
| GCTTTTTATT | TATTTTATGT | CGAGTTTTTT | AGACTACGTA | GAGCCGAATG | 100 |
| AAAATTTCAT | GTTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |

```
TGGTTTAGTA TTTTACACTG TGTATGTTCC TCTTTTAGCT TTGCGTTTTC      250

TACTTTCACT ACGATACTAC TTTTTATCTT CCAATTTCAG TTGCTTATCA      300

CCAAAATATG AAATACCAAA TTAATTGTTT AAACAGTTTT ATTAGCGATT      350

AAATTAGCAC AAAACATATG AATAGATATC ATAGTCGAAT ACAAAAATTA      400

GACAAATAAT AATACACTAA AAAACAAACT AAATTGGAGA ATTGTTTTGA      450

CAAAAAATAA AAAAAATGTC AAAGTTCCAT AAAAAGGAGG ACAAAAGAGG      500

AATATAACGA AATTATCAAC AGAAACGCAC CGAGTAAGTT TATTTCCTAT      550

GATAACGCAA AAACAAAAAA AAAATCCAAT TCCATTAGAG AGAGAGAGAG      600

AGAGAGAGAG AGAGAGAGAC TTTTTTAGAA AGTACACAAA AAAAATGAAA      650

AACTAGAGAG AGAAACAAGT GGCTAGCTAG CTCGCCAAAC TTCTTCAACA      700

ATGGCGGTTT CCTAGGGTTT GATGTTTATA TGATCGGGAA ACTCTCTCAT      750

CTAGATCGCG ATAACTCTCT TTTCCATGGA AATGCCCGGT AGAAGATCTA      800

ATTACACTTT GCTTAGTCAA TTTTCTGACG ATCAGGTGTC AGTTTCCGTC      850

ACCGGAGCTC CTCCGCCTCA CTATGATTCC TTGTCGAGCG AAAACAGGAG      900

CAACCATAAC AGCGGGAACA CCGGGAAAGC TAAGGCGGAG AGAGGCGGAT      950

TTGATTGGGA TCCTAGCGGT GGTGGTGGTG GTGATCATAG GTTGAATAAT     1000

CAACCGAATC GGGTTGGGAA TAATATGTAT GCTTCGTCTC TAGGGTTGCA     1050

AAGGCAATCC AGTGGGAGTA GTTTCGGTGA GAGCTCTTTG TCTGGGGATT     1100

ATTACATGCC TACGCTTTCT GCGGCGGCTA ACGAGATCGA ATCTGTTGGA     1150

TTTCCTCAAG ATGATGGGTT TAGGCTTGGA TTTGGTGGTG GTGGAGGAGA     1200

TTTGAGGATA CAGATGGCGG CGGACTCCGC TGGAGGGTCT TCATCTGGGA     1250

AGAGCTGGGC GCAGCAGACG GAGGAGAGTT ATCAGCTGCA GCTTGCATTG     1300

GCGTTAAGGC TTTCGTCGGA GGCTACTTGT GCCGACGATC CGAACTTTCT     1350

GGATCCTGTA CCGGACGAGT CTGCTTTACG GACTTCGCCA AGTTCAGCCG     1400

AAACCGTTTC ACATCGTTTC TGGGTATTTG TTCCTGTTAA GCTTTGTTTC     1450

CCAAAATTAT TGAATCGTGG TTATAGAGAT ATGGTCCTCT TGTTTCCGAA     1500

GTTTCAGTTA GATCTCCTTA CCAAAAGTCT ATTAGTAGCA AATGAGATAT     1550

GTTGTTTAGA TACATTGCAG AGTATGATTG TTTTGTGTGC TGCATCAGGT     1600

TAATGGCTGC TTATCGTACT ATGATAAAGT TCCTGATGGG TTTTATATGA     1650

TGAATGGTCT GGATCCCTAT ATTTGGACCT TATGCATCGA CCTGCATGAA     1700

AGTGGTCGCA TCCCTTCAAT TGAATCATTA AGAGCTGTTG ATTCTGGTGT     1750

TGATTCTTCG CTTGAAGCGA TCATAGTTGA TAGGCGTAGT GATCCAGCCT     1800

TCAAGGAACT TCACAATAGA GTCCACGACA TATCTTGTAG CTGCATTACC     1850

ACAAAGAGG TTGTTGATCA GCTGGCAAAG CTTATCTGCA ATCGTATGGG     1900

GTTTGTACTC ATACAATCCT TACTATCCCT TTGAACTTAT ATTTTTATAT     1950

CTTCCTGTGA TTTCTCACAT TGTACTCGTT AATTCTTGCT TCCCCAGGGG     2000

TCCAGTTATC ATGGGGAAG ATGAGTTGGT TCCCATGTGG AAGGAGTGCA     2050

TTGATGGTCT AAAAGAAATC TTTAAAGTGG TGGTTCCCAT AGGTAGCCTC     2100

TCTGTTGGAC TCTGCAGACA TCGAGCTTTA CTCTTCAAAG TGAGATCCCA     2150

ACTTTGATGC TATCCCCATG ACATTTAAGA CATCTTGTGA AATGATCATA     2200

TAAATTATTG TGCTTCATCC ATTTGTTTTT ATTGGAATAC ATATGAAGAA     2250
```

| | | | | |
|---|---|---|---|---|
| CGTTGAATGT | GAAAAGTGGT | GTTATTGATT | AGAAAAAAAT | AGGTTACTGA | 2300
| TAGTTGAATG | TTCCAAAGAA | AAAAGTATT | TTATATCTTC | TATTTGGTGC | 2350
| ATGCAGGTAC | TGGCTGACAT | AATTGATTTA | CCCTGTCGAA | TTGCCAAAGG | 2400
| ATGTAAATAT | TGTAATAGAG | ACGATGCCGC | TTCGTGCCTT | GTCAGGTTTG | 2450
| GGCTTGATAG | GTATGATACA | AGTGATTGCG | AAAGAGCCTT | TATTTTCCTA | 2500
| TTTTCTTTGC | TTTTGTTTC | TGGAAAAACA | ATTATAGCTC | CAAATGTTTC | 2550
| GCAGAATATT | AGGTTGATGA | CGTGGAAAAT | TTGTTTTGGT | TTCAGGGAGT | 2600
| ACCTGGTTGA | TTTAGTAGGA | AAGCCAGGTC | ACTTATGGGA | GCCTGATTCC | 2650
| TTGCTAAATG | GTCCTTCATC | TATCTCAATT | TCTTCTCCTC | TGCGGTTTCC | 2700
| ATGACCAAAG | CCAGTTGAAC | CCGCAGTCGA | TTTTAGGTTA | CTAGCCAAAC | 2750
| AATATTTCTC | CGATAGCCAG | TCTCTTAATC | TTGTTTTCGA | TCCTGCATCA | 2800
| GGTATTCCCA | TACAAAAAAC | CTAAATAATA | TGTTAACTTT | TTGCATGCTG | 2850
| CTTACATCTC | GTTTGTATT | TCCCCTAAAA | GAGTAATCTC | CTATCATTTA | 2900
| GGGTATTTCT | TGATCATGTC | TCAGTATCTG | AAGTGTTAGT | AGTCTTAGAA | 2950
| TGATTCTATT | GTTTGTTTTC | TTGTCTCTTT | TCACTTTAGT | TGTTTTGGC | 3000
| TGTTGATGTG | TATGTTTGTT | GGTGGGTTCT | TTGCCTAATG | ATATTTAAGG | 3050
| TTAAACTTGT | TAGTCTGCTG | TTCAAGCTTA | TGAATTCTAG | TGCATTTATG | 3100
| TGCAAGACTT | GTCTTCTGGA | CTCTAATTTC | TTATATCTGC | TTGTTTGAAT | 3150
| GGTTGTAGAT | GATATGGGAT | TCTCAATGTT | TCATAGGCAA | ATGATAATC | 3200
| CGGGTGGAGA | GAATGACGCA | TTGGCAGAAA | ATGGTGGTGG | GTCTTTGCCA | 3250
| CCCAGTGCTA | ATATGCCTCC | ACAGAACATG | ATGCGTGCGT | CAAATCAAAT | 3300
| TGAAGCAGCA | CCTATGAATG | CCCCACCAAT | CAGTCAGCCA | GTTCCAAACA | 3350
| GGGCAAATAG | GAACTTGGA | CTTGATGGTG | ATGATATGGA | CATCCCGTGG | 3400
| TGTGATCTTA | ATATAAAAGA | AAAGATTGGA | GCAGGTAATA | ATTTTACGGA | 3450
| AAAATTAATG | ATTCGGTCTA | AAAATGCAAA | GAAATATGAA | ATTCTTGAGG | 3500
| AAGTGGTTTT | GCTTGGACT | CTGTTCTCGA | ACAAAATAAG | GAAAAAGTGC | 3550
| CACCCATTTT | GAGATTACAT | TCTTCTCTGT | TGCCTTTAAT | TCTTCCACTC | 3600
| TAATTTGAGC | GACTGCTCTT | TCAGGTTCCT | TTGGCACTGT | CCACCGTGCT | 3650
| GAGTGGCATG | GCTCGGTAAG | AACTTTTTTG | TCAGAATTTA | CGCAGCTGAA | 3700
| TTTTTTTCG | CTCTAAAAAT | TTGGTTGTGA | CTTTTGGATC | TGCTTGGTAT | 3750
| TATAAAAGGC | AAAGTTATTG | TATATGTGAC | TCTCCGTTCT | GTCAGAAATT | 3800
| AAACACGGAC | AAAAGGTGTC | CCATTTTAGA | TGTATATGTG | TCTTTATATC | 3850
| ATAAATTTGT | CTTCCTGTTT | GAATTTTACA | ATTCTATCAC | TAGAAGAATT | 3900
| CTAATTTTGA | TTATTGCAGT | AATATTCTCT | ATCAATTTCA | GGATGTTGCT | 3950
| GTGAAAATTC | TCATGGAGCA | AGACTTCCAT | GCTGAGCGTG | TTAATGAGTT | 4000
| CTTAAGAGAG | GTGCACAAAT | AAAATTTTCT | CTTGATTTTG | GTAATGAACT | 4050
| TGTTGTATTA | ATGTCTCCAA | TGATCTTGAT | TCGCTGTCAG | GTTGCGATAA | 4100
| TGAAACGCCT | TCGCCACCCT | AACATTGTTC | TCTTCATGGG | TGCGGTCACT | 4150
| CAACCTCCAA | ATTTGTCAAT | AGTGACAGAA | TATTTGTCAA | GGTACAATTA | 4200
| CTTGGATTTG | GAAGGTTTGA | TGTACTGAGT | GTAGAATTTT | GGCCTATAAT | 4250
| GACTCTAATA | CCATGATTTC | TTTCAAACAG | AGGTAGTTTA | TACAGACTTT | 4300

```
TGCATAAAAG TGGAGCAAGG GAGCAATTAG ATGAGAGACG TCGCCTGAGT       4350
ATGGCTTATG ATGTGGTATG TTTAACTCCT TATGTTACAT GTATGGGTGA       4400
TTACTTCCTG ATCTTGGTGT TCTTCACAT  GGAACTTTCT TTCCAATTCT       4450
CTGTCACAGG CTAAGGGAAT GAATTATCTT CACAATCGCA ATCCTCCAAT       4500
TGTGCATAGA GATCTAAAAT CTCCAAACTT ATTGGTTGAC AAAAAATATA       4550
CAGTCAAGGT TTGAATCTAA ATTAGAAATT GTTGTGTCCA ATGTTTTGAT       4600
TTTGATATTT TATTCCTCTT GTGAGACAAG CTTATATATA AATTATGATT       4650
TTTAATTCTA AATTGGTTTG GAGACATTAC AAAAAGGCGT TAATCTGCTG       4700
AAACTTAAAA GATACAGCAG CCTCAAGCTG TCGTCTTAAA AACAATCAGA       4750
ACATTATTAT TCTAACTCCT CAATTTGTCT TGAAATTTCA GGTTTGTGAT       4800
TTTGGTCTCT CGCGATTGAA GGCCAGCACG TTTCTTTCCT CGAAGTCAGC       4850
AGCTGGAACC GTAAGTTCAG TTTGTTTGAA ACTAAACAC  GCTGAACAAC       4900
GTAACTTTCT TCTAGGTCCT ATTTCCAATG GAAGCTAAAT AATTACTGAC       4950
TTTGATATAT CAGCCCGAGT GGATGGCACC AGAAGTCCTG CGAGATGAGC       5000
CGTCTAATGA AAAGTCAGAT GTGTACAGCT TCGGGGTCAT CTTGTGGGAG       5050
CTTGCTACAT TGCAACAACC ATGGGGTAAC TTAAATCCGG CTCAGGTACT       5100
TCCCACTCTA AACATCCCAA ATAATAATGA TATTATTTTG CATTTGGAAG       5150
TCCCTCACTC TACATTTCAT AACATGCTAT ATATGATCAT CCAACAAAAT       5200
GTTCCATAGG TTGTAGCTGC GGTTGGTTTC AAGTGTAAAC GGCTGGAGAT       5250
CCCGCGTAAT CTGAATCCTC AGGTTGCAGC CATAATCGAG GGTTGTTGGA       5300
CCAAGTACGT TAAGATTTTC TATCTCTTTT TTGAATTCTT CTTGAATAGA       5350
CTTCATGTTT ATGTATGTGT TCATTACCA  GTGAGCCATG GAAGCGTCCA       5400
TCATTTGCAA CTATAATGGA CTTGCTAAGA CCATTGATCA AATCAGCGGT       5450
TCCTCCGCCC AACCGCTCGG ATTTGTAAAA TACCCCGGT  CCATTCAAAA       5500
GTTGTTATAA TCATGATATG CACATATACT CTCAGCATTC TTTTGCTGCC       5550
CAGGAGGGAG ACACTAGTTA AGATATAGCT TTAAAGGTAC ATTCCTCATG       5600
AGCTATCAAT CATATCCTAC AGAATCCCAT GGTTTTTATA CATGTATTAT       5650
TTTTGCGATC TTTGTCTGCTG TTTTGTTCC CTTTTTAATG TTGCAGATTG       5700
TTAAAATGTA CATGACTATT GTCACAGGGA GGAAAAAAA  ATGTAGTAAT       5750
GGAAACAATG TGAGGGATAT AATCTATCTA TCTAGTCCCA AAGGGTAAGC       5800
AATATTGTGT TGTTATGTCT TTGTAGCAAT GCACTGAAAG CTATATTTAA       5850
TTACATTGCT GTACATTTAT ACCGCTAAAT TAGTTACTAA GCGAAGGTAA       5900
AAAAGAGCAG CTGGTAAATG CTGTCAAAGG GTTTTGCAAA CTCAATATGA       5950
TTCATTGGAT TTACATTTGT TCACTGTGCG ATTAGTCTGG ACTATAAACC       6000
AACAGAAATG AAATAAGACT GTAACTTTCG GAGACTCTAA TACAGATGAA       6050
TATAATCCCA AATCGTTAAA AACGCATTGG GACTGAAAAT ATCTAGATAC       6100
ATAGTCAACT ATTTTGCCT  TCGCGTCTAA GTAAGTTCCC ACACTTGAAA       6150
ACGACTTTAC CTGTCTTCCG AATTAATCGT TTGATGGATC GGTAACCAAT       6200
AGGATTGCGT AAATCAAAAT TATACAATAT TAAATTCTGA AAAAGGAAAC       6250
ACGAAAAGCG AATCAGTGAT TTGTGAGGGC CCAGTTCCAA ATTAGAAAGC       6300
TGACCTGGCA AA                                                6312
```

( 2 ) INFORMATION FOR SEQ ID NO:6:

( i ) SEQUENCE CHARACTERISTICS:
    ( A ) LENGTH: 6312 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
| TATAGTCCAT | TCTCTCACTT | TCTATTCTAA | ATATTGTGGA | CGTTATAAAG | 50 |
| GCTTTTATT | TATTTTATGT | CGAGTTTTTT | AGACTACGTA | GAGCCGAATG | 100 |
| AAAATTTCAT | GTTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |
| TGGTTTAGTA | TTTTACACTG | TGTATGTTCC | TCTTTTAGCT | TTGCGTTTTC | 250 |
| TACTTTCACT | ACGATACTAC | TTTTTATCTT | CCAATTTCAG | TTGCTTATCA | 300 |
| CCAAAATATG | AAATACCAAA | TTAATTGTTT | AAACAGTTTT | ATTAGCGATT | 350 |
| AAATTAGCAC | AAAACATATG | AATAGATATC | ATAGTCGAAT | ACAAAAATTA | 400 |
| GACAAATAAT | AATACACTAA | AAAACAAACT | AAATTGGAGA | ATTGTTTTGA | 450 |
| CAAAAAATAA | AAAAAATGTC | AAAGTTCCAT | AAAAAGGAGG | ACAAAAGAGG | 500 |
| AATATAACGA | AATTATCAAC | AGAAACGCAC | CGAGTAAGTT | TATTTCCTAT | 550 |
| GATAACGCAA | AAACAAAAAA | AAAATCCAAT | TCCATTAGAG | AGAGAGAGAG | 600 |
| AGAGAGAGAG | AGAGAGAGAC | TTTTTTAGAA | AGTACACAAA | AAAAATGAAA | 650 |
| AACTAGAGAG | AGAAACAAGT | GGCTAGCTAG | CTCGCCAAAC | TTCTTCAACA | 700 |
| ATGGCGGTTT | CCTAGGGTTT | GATGTTTATA | TGATCGGGAA | ACTCTCTCAT | 750 |
| CTAGATCGCG | ATAACTCTCT | TTTCCATGGA | AATGCCCGGT | AGAAGATCTA | 800 |
| ATTACACTTT | GCTTAGTCAA | TTTTCTGACG | ATCAGGTGTC | AGTTTCCGTC | 850 |
| ACCGGAGCTC | CTCCGCCTCA | CTATGATTCC | TTGTCGAGCG | AAAACAGGAG | 900 |
| CAACCATAAC | AGCGGGAACA | CCGGGAAAGC | TAAGGCGGAG | AGAGGCGGAT | 950 |
| TTGATTGGGA | TCCTAGCGGT | GGTGGTGGTG | GTGATCATAG | GTTGAATAAT | 1000 |
| CAACCGAATC | GGGTTGGGAA | TAATATGTAT | GCTTCGTCTC | TAGGGTTGCA | 1050 |
| AAGGCAATCC | AGTGGGAGTA | GTTTCGGTGA | GAGCTCTTTG | TCTGGGGATT | 1100 |
| ATTACATGCC | TACGCTTTCT | GCGGCGGCTA | ACGAGATCGA | ATCTGTTGGA | 1150 |
| TTTCCTCAAG | ATGATGGGTT | TAGGCTTGGA | TTTGGTGGTG | GTGGAGGAGA | 1200 |
| TTTGAGGATA | CAGATGGCGG | CGGACTCCGC | TGGAGGGTCT | TCATCTGGGA | 1250 |
| AGAGCTGGGC | GCAGCAGACG | GAGGAGAGTT | ATCAGCTGCA | GCTTGCATTG | 1300 |
| GCGTTAAGGC | TTTCGTCGGA | GGCTACTTGT | GCCGACGATC | CGAACTTTCT | 1350 |
| GGATCCTGTA | CCGGACGAGT | CTGCTTTACG | GACTTCGCCA | AGTTCAGCCG | 1400 |
| AAACCGTTTC | ACATCGTTTC | TGGGTATTTG | TTCCTGTTAA | GCTTTGTTTC | 1450 |
| CCAAAATTAT | TGAATCGTGG | TTATAGAGAT | ATGGTCCTCT | TGTTTCCGAA | 1500 |
| GTTTCAGTTA | GATCTCCTTA | CCAAAAGTCT | ATTAGTAGCA | AATGAGATAT | 1550 |
| GTTGTTTAGA | TACATTGCAG | AGTATGATTG | TTTTGTGTGC | TGCATCAGGT | 1600 |
| TAATGGCTGC | TTATCGTACT | ATGATAAAGT | TCCTGATGGG | TTTTATATGA | 1650 |
| TGAATGGTCT | GGATCCCTAT | ATTTGGACCT | TATGCATCGA | CCTGCATGAA | 1700 |
| AGTGGTCGCA | TCCCTTCAAT | TGAATCATTA | AGAGCTGTTG | ATTCTGGTGT | 1750 |

```
TGATTCTTCG CTTGAAGCGA TCATAGTTGA TAGGCGTAGT GATCCAGCCT   1800
TCAAGGAACT TCACAATAGA GTCCACGACA TATCTTGTAG CTGCATTACC   1850
ACAAAAGAGG TTGTTGATCA GCTGGCAAAG CTTATCTGCA ATCGTATGGG   1900
GTTTGTACTC ATACAATCCT TACTATCCCT TTGAACTTAT ATTTTTATAT   1950
CTTCCTGTGA TTTCTCACAT TGTACTCGTT AATTCTTGCT TCCCCAGGGG   2000
TCCAGTTATC ATGGGGAAG  ATGAGTTGGT TCCCATGTGG AAGGAGTGCA   2050
TTGATGGTCT AAAAGAAATC TTTAAAGTGG TGGTTCCCAT AGGTAGCCTC   2100
TCTGTTGGAC TCTGCAGACA TCGAGCTTTA CTCTTCAAAG TGAGATCCCA   2150
ACTTTGATGC TATCCCCATG ACATTTAAGA CATCTTGTGA AATGATCATA   2200
TAAATTATTG TGCTTCATCC ATTTGTTTTT ATTGGAATAC ATATGAAGAA   2250
CGTTGAATGT GAAAAGTGGT GTTATTGATT AGAAAAAAAT AGGTTACTGA   2300
TAGTTGAATG TTCCAAAGAA AAAAGTATT  TTATATCTTC TATTTGGTGC   2350
ATGCAGGTAC TGGCTGACAT AATTGATTTA CCCTGTCGAA TTGCCAAAGG   2400
ATGTAAATAT TGTAATAGAG ACGATGCCGC TTCGTGCCTT GTCAGGTTTG   2450
GGCTTGATAG GTATGATACA AGTGATTGCG AAAGAGCCTT TATTTTCCTA   2500
TTTTCTTTGC TTTTTGTTTC TGGAAAAACA ATTATAGCTC CAAATGTTTC   2550
GCAGAATATT AGGTTGATGA CGTGGAAAAT TGTTTTGGT  TTCAGGGAGT   2600
ACCTGGTTGA TTAGTAGGA  AAGCCAGGTC ACTTATGGGA GCCTGATTCC   2650
TTGCTAAATG GTCCTTCATC TATCTCAATT TCTTCTCCTC TGCGGTTTCC   2700
ACGACCAAAG CCAGTTGAAC CCGCAGTCGA TTTTAGGTTA CTAGCCAAAC   2750
AATATTTCTC CGATAGCCAG TCTCTTAATC TTGTTTTCGA TCCTGCATCA   2800
GGTATTCCCA TACAAAAAAC CTAAATAATA TGTTAACTTT TTGCATGCTG   2850
CTTACATCTC GTTTTGTATT TCCCTAAAA  GAGTAATCTC CTATCATTTA   2900
GGGTATTTCT TGATCATGTC TCAGTATCTG AAGTGTTAGT AGTCTTAGAA   2950
TGATTCTATT GTTTGTTTTC TTGTCTCTTT TCACTTTAGT TGTTTTGGC   3000
TGTTGATGTG TATGTTTGTT GGTGGGTTCT TTGCCTAATG ATATTTAAGG   3050
TTAAACTTGT TAGTCTGCTG TTCAAGCTTA TGAATTCTAG TGCATTTATG   3100
TGCAAGACTT GTCTTCTGGA CTCTAATTTC TTATATCTGC TTGTTTGAAT   3150
GGTTGTAGAT GATATGGGAT TCTCAATGTT TCATAGGCAA TATGATAATC   3200
CGGGTGGAGA GAATGACGCA TTGGCAGAAA ATGGTGGTGG GTCTTTGCCA   3250
CCCAGTGCTA ATATGCCTCC ACAGAACATG ATGCGTGCGT CAAATCAAAT   3300
TGAAGCAGCA CCTATGAATG CCCCACCAAT CAGTCAGCCA GTTCCAAACA   3350
GGGCAAATAG GGAACTTGGA CTTGATGGTG ATGATATGGA CATCCCGTGG   3400
TGTGATCTTA ATATAAAAGA AAAGATTGGA GCAGGTAATA ATTTTACGGA   3450
AAAATTAATG ATTCGGTCTA AAAATGCAAA GAAATATGAA ATTCTTGAGG   3500
AAGTGGTTTT GCTTTGGACT CTGTTCTCGA ACAAAATAAG GAAAAAGTGC   3550
CACCCATTTT GAGATTACAT TCTTCTCTGT TGCCTTTAAT TCTTCCACTC   3600
TAATTTGAGC GACTGCTCTT TCAGGTTCCT TTGGCACTGT CCACCGTGCT   3650
GAGTGGCATG GCTCGGTAAG AACTTTTTTG TCAGAATTTA CGCAGCTGAA   3700
TTTTTTTTCG CTCTAAAAAT TTGGTTGTGA CTTTTGGATC TGCTTGGTAT   3750
TATAAAAGGC AAAGTTATTG TATATGTGAC TCTCCGTTCT GTCAGAAATT   3800
```

| | | | | | |
|---|---|---|---|---|---|
| AAACACGGAC | AAAAGGTGTC | CCATTTTAGA | TGTATATGTG | TCTTTATATC | 3850 |
| ATAAATTTGT | CTTCCTGTTT | GAATTTTACA | ATTCTATCAC | TAGAAGAATT | 3900 |
| CTAATTTTGA | TTATTGCAGT | AATATTCTCT | ATCAATTTCA | GGATGTTGCT | 3950 |
| GTGAAAATTC | TCATGGAGCA | AGACTTCCAT | GCTGAGCGTG | TTAATGAGTT | 4000 |
| CTTAAGAGAG | GTGCACAAAT | AAAATTTCT | CTTGATTTTG | GTAATGAACT | 4050 |
| TGTTGTATTA | ATGTCTCCAA | TGATCTTGAT | TCGCTGTCAG | GTTGCGATAA | 4100 |
| TGAAACGCCT | TCGCCACCCT | AACATTGTTC | TCTTCATGGG | TGCGGTCACT | 4150 |
| CAACCTCCAA | ATTTGTCAAT | AGTGACAGAA | TATTTGTCAA | GGTACAATTA | 4200 |
| CTTGGATTTG | GAAGGTTTGA | TGTACTGAGT | GTAGAATTTT | GGCCTATAAT | 4250 |
| GACTCTAATA | CCATGATTTC | TTTCAAACAG | AGGTAGTTTA | TACAGACTTT | 4300 |
| TGCATAAAAG | TGGAGCAAGG | GAGCAATTAG | ATGAGAGACG | TCGCCTGAGT | 4350 |
| ATGGCTTATG | ATGTGGTATG | TTTAACTCCT | TATGTTACAT | GTATGGGTGA | 4400 |
| TTACTTCCTG | ATCTTGGTGT | TTCTTCACAT | GGAACTTTCT | TTCCAATTCT | 4450 |
| CTGTCACAGG | CTAAGGGAAT | GAATTATCTT | CACAATCGCA | ATCCTCCAAT | 4500 |
| TGTGCATAGA | GATCTAAAAT | CTCCAAACTT | ATTGGTTGAC | AAAAAATATA | 4550 |
| CAGTCAAGGT | TTGAATCTAA | ATTAGAAATT | GTTGTGTCCA | ATGTTTTGAT | 4600 |
| TTTGATATTT | TATTCCTCTT | GTGAGACAAG | CTTATATATA | AATTATGATT | 4650 |
| TTTAATTCTA | AATTGGTTTG | GAGACATTAC | AAAAAGGCGT | TAATCTGCTG | 4700 |
| AAACTTAAAA | GATACAGCAG | CCTCAAGCTG | TCGTCTTAAA | AACAATCAGA | 4750 |
| ACATTATTAT | TCTAACTCCT | CAATTTGTCT | TGAAATTTCA | GGTTTGTGAA | 4800 |
| TTTGGTCTCT | CGCGATTGAA | GGCCAGCACG | TTTCTTTCCT | CGAAGTCAGC | 4850 |
| AGCTGGAACC | GTAAGTTCAG | TTTGTTTGAA | ACTAAAACAC | GCTGAACAAC | 4900 |
| GTAACTTTCT | TCTAGGTCCT | ATTTCCAATG | GAAGCTAAAT | AATTACTGAC | 4950 |
| TTTGATATAT | CAGCCCGAGT | GGATGGCACC | AGAAGTCCTG | CGAGATGAGC | 5000 |
| CGTCTAATGA | AAAGTCAGAT | GTGTACAGCT | TCGGGGTCAT | CTTGTGGGAG | 5050 |
| CTTGCTACAT | TGCAACAACC | ATGGGGTAAC | TTAAATCCGG | CTCAGGTACT | 5100 |
| TCCCACTCTA | AACATCCCAA | ATAATAATGA | TATTATTTTG | CATTTGGAAG | 5150 |
| TCCCTCACTC | TACATTTCAT | AACATGCTAT | ATATGATCAT | CCAACAAAAT | 5200 |
| GTTCCATAGG | TTGTAGCTGC | GGTTGGTTTC | AAGTGTAAAC | GGCTGGAGAT | 5250 |
| CCCGCGTAAT | CTGAATCCTC | AGGTTGCAGC | CATAATCGAG | GGTTGTTGGA | 5300 |
| CCAAGTACGT | TAAGATTTTC | TATCTCTTTT | TTGAATTCTT | CTTGAATAGA | 5350 |
| CTTCATGTTT | ATGTATGTGT | TTCATTACCA | GTGAGCCATG | GAAGCGTCCA | 5400 |
| TCATTTGCAA | CTATAATGGA | CTTGCTAAGA | CCATTGATCA | AATCAGCGGT | 5450 |
| TCCTCCGCCC | AACCGCTCGG | ATTTGTAAAA | TACCCCGGT | CCATTCAAAA | 5500 |
| GTTGTTATAA | TCATGATATG | CACATATACT | CTCAGCATTC | TTTTGCTGCC | 5550 |
| CAGGAGGGAG | ACACTAGTTA | AGATATAGCT | TTAAAGGTAC | ATTCCTCATG | 5600 |
| AGCTATCAAT | CATATCCTAC | AGAATCCCAT | GGTTTTTATA | CATGTATTAT | 5650 |
| TTTTGCGATC | TTTGTCTGCTG | TTTTGTTCC | CTTTTAATG | TTGCAGATTG | 5700 |
| TTAAAATGTA | CATGACTATT | GTCACAGGGA | GGAAAAAAAA | ATGTAGTAAT | 5750 |
| GGAAACAATG | TGAGGGATAT | AATCTATCTA | TCTAGTCCCA | AAGGGTAAGC | 5800 |
| AATATTGTGT | TGTTATGTCT | TTGTAGCAAT | GCACTGAAAG | CTATATTTAA | 5850 |

-continued

| | | | | | |
|---|---|---|---|---|---|
| TTACATTGCT | GTACATTTAT | ACCGCTAAAT | TAGTTACTAA | GCGAAGGTAA | 5900 |
| AAAAGAGCAG | CTGGTAAATG | CTGTCAAAGG | GTTTTGCAAA | CTCAATATGA | 5950 |
| TTCATTGGAT | TTACATTTGT | TCACTGTGCG | ATTAGTCTGG | ACTATAAACC | 6000 |
| AACAGAAATG | AAATAAGACT | GTAACTTTCG | GAGACTCTAA | TACAGATGAA | 6050 |
| TATAATCCCA | AATCGTTAAA | AACGCATTGG | GACTGAAAAT | ATCTAGATAC | 6100 |
| ATAGTCAACT | ATTTTGCCT | TCGCGTCTAA | GTAAGTCCC | ACACTTGAAA | 6150 |
| ACGACTTTAC | CTGTCTTCCG | AATTAATCGT | TTGATGGATC | GGTAACCAAT | 6200 |
| AGGATTGCGT | AAATCAAAAT | TATACAATAT | TAAATTCTGA | AAAAGGAAAC | 6250 |
| ACGAAAAGCG | AATCAGTGAT | TTGTGAGGGC | CCAGTTCCAA | ATTAGAAAGC | 6300 |
| TGACCTGGCA | AA | | | | 6312 |

(2) INFORMATION FOR SEQ ID NO:7:

(i) SEQUENCE CHARACTERISTICS:
(A) LENGTH: 6312 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

| | | | | | |
|---|---|---|---|---|---|
| TATAGTCCAT | TCTCTCACTT | TCTATTCTAA | ATATTGTGGA | CGTTATAAAG | 50 |
| GCTTTTTATT | TATTTTATGT | CGAGTTTTTT | AGACTACGTA | GAGCCGAATG | 100 |
| AAAATTTCAT | GTTTAGGTAT | ACGAAACTTG | GATCCAATGT | TACGGATTCA | 150 |
| GATTGGTGTA | AAAGATCAAA | TTTGATAGTA | TTTGGATTTG | ATAGGCAAGA | 200 |
| TGGTTTAGTA | TTTTACACTG | TGTATGTTCC | TCTTTTAGCT | TTGCGTTTTC | 250 |
| TACTTTCACT | ACGATACTAC | TTTTTATCTT | CCAATTTCAG | TTGCTTATCA | 300 |
| CCAAAATATG | AAATACCAAA | TTAATTGTTT | AAACAGTTTT | ATTAGCGATT | 350 |
| AAATTAGCAC | AAAACATATG | AATAGATATC | ATAGTCGAAT | ACAAAAATTA | 400 |
| GACAAATAAT | AATACACTAA | AAAACAAACT | AAATTGGAGA | ATTGTTTTGA | 450 |
| CAAAAAATAA | AAAAAATGTC | AAAGTTCCAT | AAAAAGGAGG | ACAAAAGAGG | 500 |
| AATATAACGA | AATTATCAAC | AGAAACGCAC | CGAGTAAGTT | TATTTCCTAT | 550 |
| GATAACGCAA | AAACAAAAAA | AAAATCCAAT | TCCATTAGAG | AGAGAGAGAG | 600 |
| AGAGAGAGAG | AGAGAGAGAC | TTTTTTAGAA | AGTACACAAA | AAAAATGAAA | 650 |
| AACTAGAGAG | AGAAACAAGT | GGCTAGCTAG | CTCGCCAAAC | TTCTTCAACA | 700 |
| ATGGCGGTTT | CCTAGGGTTT | GATGTTTATA | TGATCGGGAA | ACTCTCTCAT | 750 |
| CTAGATCGCG | ATAACTCTCT | TTTCCATGGA | AATGCCCGGT | AGAAGATCTA | 800 |
| ATTACACTTT | GCTTAGTCAA | TTTTCTGACG | ATCAGGTGTC | AGTTTCCGTC | 850 |
| ACCGGAGCTC | CTCCGCCTCA | CTATGATTCC | TTGTCGAGCG | AAAACAGGAG | 900 |
| CAACCATAAC | AGCGGGAACA | CCGGGAAAGC | TAAGGCGGAG | AGAGGCGGAT | 950 |
| TTGATTGGGA | TCCTAGCGGT | GGTGGTGGTG | GTGATCATAG | GTTGAATAAT | 1000 |
| CAACCGAATC | GGGTTGGGAA | TAATATGTAT | GCTTCGTCTC | TAGGGTTGCA | 1050 |
| AAGGCAATCC | AGTGGGAGTA | GTTTCGGTGA | GAGCTCTTTG | TCTGGGGATT | 1100 |
| ATTACATGCC | TACGCTTTCT | GCGGCGGCTA | ACGAGATCGA | ATCTGTTGGA | 1150 |
| TTTCCTCAAG | ATGATGGGTT | TAGGCTTGGA | TTTGGTGGTG | GTGGAGGAGA | 1200 |

| | | | | |
|---|---|---|---|---|
| TTTGAGGATA | CAGATGGCGG | CGGACTCCGC | TGGAGGGTCT | TCATCTGGGA | 1250
| AGAGCTGGGC | GCAGCAGACG | GAGGAGAGTT | ATCAGCTGCA | GCTTGCATTG | 1300
| GCGTTAAGGC | TTTCGTCGGA | GGCTACTTGT | GCCGACGATC | CGAACTTTCT | 1350
| GGATCCTGTA | CCGGACGAGT | CTGCTTTACG | GACTTCGCCA | AGTTCAGCCG | 1400
| AAACCGTTTC | ACATCGTTTC | TGGGTATTTG | TTCCTGTTAA | GCTTTGTTTC | 1450
| CCAAAATTAT | TGAATCGTGG | TTATAGAGAT | ATGGTCCTCT | TGTTTCCGAA | 1500
| GTTTCAGTTA | GATCTCCTTA | CCAAAAGTCT | ATTAGTAGCA | AATGAGATAT | 1550
| GTTGTTTAGA | TACATTGCAG | AGTATGATTG | TTTTGTGTGC | TGCATCAGGT | 1600
| TAATGGCTGC | TTATCGTACT | ATGATAAAGT | TCCTGATGGG | TTTTATATGA | 1650
| TGAATGGTCT | GGATCCCTAT | ATTTGGACCT | TATGCATCGA | CCTGCATGAA | 1700
| AGTGGTCGCA | TCCCTTCAAT | TGAATCATTA | AGAGCTGTTG | ATTCTGGTGT | 1750
| TGATTCTTCG | CTTGAAGCGA | TCATAGTTGA | TAGGCGTAGT | GATCCAGCCT | 1800
| TCAAGGAACT | TCACAATAGA | GTCCACGACA | TATCTTGTAG | CTGCATTACC | 1850
| ACAAAGAGG | TTGTTGATCA | GCTGGCAAAG | CTTATCTGCA | ATCGTATGGG | 1900
| GTTTGTACTC | ATACAATCCT | TACTATCCCT | TTGAACTTAT | ATTTTTATAT | 1950
| CTTCCTGTGA | TTTCTCACAT | TGTACTCGTT | AATTCTTGCT | TCCCCAGGGG | 2000
| TCCAGTTATC | ATGGGGAAG | ATGAGTTGGT | TCCCATGTGG | AAGGAGTGCA | 2050
| TTGATGGTCT | AAAAGAAATC | TTTAAAGTGG | TGGTTCCCAT | AGGTAGCCTC | 2100
| TCTGTTGGAC | TCTGCAGACA | TCGAGCTTTA | CTCTTCAAAG | TGAGATCCCA | 2150
| ACTTTGATGC | TATCCCCATG | ACATTTAAGA | CATCTTGTGA | AATGATCATA | 2200
| TAAATTATTG | TGCTTCATCC | ATTTGTTTTT | ATTGGAATAC | ATATGAAGAA | 2250
| CGTTGAATGT | GAAAAGTGGT | GTTATTGATT | AGAAAAAAAT | AGGTTACTGA | 2300
| TAGTTGAATG | TTCCAAAGAA | AAAAAGTATT | TTATATCTTC | TATTTGGTGC | 2350
| ATGCAGGTAC | TGGCTGACAT | AATTGATTTA | CCCTGTCGAA | TTGCCAAAGG | 2400
| ATGTAAATAT | TGTAATAGAG | ACGATGCCGC | TTCGTGCCTT | GTCAGGTTTG | 2450
| GGCTTGATAG | GTATGATACA | AGTGATTGCG | AAAGAGCCTT | TATTTCCTA | 2500
| TTTTCTTTGC | TTTTTGTTTC | TGGAAAAACA | ATTATAGCTC | CAAATGTTTC | 2550
| GCAGAATATT | AGGTTGATGA | CGTGGAAAAT | TTGTTTTGGT | TTCAGGGAGT | 2600
| ACCTGGTTGA | TTTAGTAGGA | AAGCCAGGTC | ACTTATGGGA | GCCTGATTCC | 2650
| TTGCTAAATG | GTCCTTCATC | TATCTCAATT | TCTTCTCCTC | TGCGGTTTCC | 2700
| ACGACCAAAG | CCAGTTGAAC | CCGCAGTCGA | TTTTAGGTTA | CTAGCCAAAC | 2750
| AATATTTCTC | CGATAGCCAG | TCTCTTAATC | TTGTTTTCGA | TCCTGCATCA | 2800
| GGTATTCCCA | TACAAAAAAC | CTAAATAATA | TGTTAACTTT | TTGCATGCTG | 2850
| CTTACATCTC | GTTTTGTATT | TCCCCTAAAA | GAGTAATCTC | CTATCATTTA | 2900
| GGGTATTTCT | TGATCATGTC | TCAGTATCTG | AAGTGTTAGT | AGTCTTAGAA | 2950
| TGATTCTATT | GTTTGTTTTC | TTGTCTCTTT | TCACTTTAGT | TGTTTTTGGC | 3000
| TGTTGATGTG | TATGTTTGTT | GGTGGGTTCT | TTGCCTAATG | ATATTTAAGG | 3050
| TTAAACTTGT | TAGTCTGCTG | TTCAAGCTTA | TGAATTCTAG | TGCATTTATG | 3100
| TGCAAGACTT | GTCTTCTGGA | CTCTAATTTC | TTATATCTGC | TTGTTTGAAT | 3150
| GGTTGTAGAT | GATATGGGAT | TCTCAATGTT | TCATAGGCAA | TATGATAATC | 3200
| CGGGTGGAGA | GAATGACGCA | TTGGCAGAAA | ATGGTGGTGG | GTCTTTGCCA | 3250

| | | | | | |
|---|---|---|---|---|---|
| CCCAGTGCTA | ATATGCCTCC | ACAGAACATG | ATGCGTGCGT | CAAATCAAAT | 3300 |
| TGAAGCAGCA | CCTATGAATG | CCCCACCAAT | CAGTCAGCCA | GTTCCAAACA | 3350 |
| GGGCAAATAG | GAACTTGGA | CTTGATGGTG | ATGATATGGA | CATCCCGTGG | 3400 |
| TGTGATCTTA | ATATAAAAGA | AAAGATTGGA | GCAGGTAATA | ATTTTACGGA | 3450 |
| AAAATTAATG | ATTCGGTCTA | AAAATGCAAA | GAAATATGAA | ATTCTTGAGG | 3500 |
| AAGTGGTTTT | GCTTTGGACT | CTGTTCTCGA | ACAAATAAG | GAAAAGTGC | 3550 |
| CACCCATTTT | GAGATTACAT | TCTTCTCTGT | TGCCTTTAAT | TCTTCCACTC | 3600 |
| TAATTTGAGC | GACTGCTCTT | TCAGGTTCCT | TTGGCACTGT | CCACCGTGCT | 3650 |
| GAGTGGCATG | GCTCGGTAAG | AACTTTTTG | TCAGAATTTA | CGCAGCTGAA | 3700 |
| TTTTTTTTCG | CTCTAAAAAT | TTGGTTGTGA | CTTTTGGATC | TGCTTGGTAT | 3750 |
| TATAAAAGGC | AAAGTTATTG | TATATGTGAC | TCTCCGTTCT | GTCAGAAATT | 3800 |
| AAACACGGAC | AAAAGGTGTC | CCATTTTAGA | TGTATATGTG | TCTTTATATC | 3850 |
| ATAAATTTGT | CTTCCTGTTT | GAATTTTACA | ATTCTATCAC | TAGAAGAATT | 3900 |
| CTAATTTTGA | TTATTGCAGT | AATATTCTCT | ATCAATTTCA | GGATGTTGCT | 3950 |
| GTGAAAATTC | TCATGGAGCA | AGACTTCCAT | GCTGAGCGTG | TTAATGAGTT | 4000 |
| CTTAAGAAAG | GTGCACAAAT | AAAATTTTCT | CTTGATTTTG | GTAATGAACT | 4050 |
| TGTTGTATTA | ATGTCTCCAA | TGATCTTGAT | TCGCTGTCAG | GTTGCGATAA | 4100 |
| TGAAACGCCT | TCGCCACCCT | AACATTGTTC | TCTTCATGGG | TGCGGTCACT | 4150 |
| CAACCTCCAA | ATTTGTCAAT | AGTGACAGAA | TATTTGTCAA | GGTACAATTA | 4200 |
| CTTGGATTTG | GAAGGTTTGA | TGTACTGAGT | GTAGAATTTT | GGCCTATAAT | 4250 |
| GACTCTAATA | CCATGATTTC | TTTCAAACAG | AGGTAGTTTA | TACAGACTTT | 4300 |
| TGCATAAAAG | TGGAGCAAGG | GAGCAATTAG | ATGAGAGACG | TCGCCTGAGT | 4350 |
| ATGGCTTATG | ATGTGGTATG | TTTAACTCCT | TATGTTACAT | GTATGGGTGA | 4400 |
| TTACTTCCTG | ATCTTGGTGT | TTCTTCACAT | GGAACTTTCT | TTCCAATTCT | 4450 |
| CTGTCACAGG | CTAAGGGAAT | GAATTATCTT | CACAATCGCA | ATCCTCCAAT | 4500 |
| TGTGCATAGA | GATCTAAAAT | CTCCAAACTT | ATTGGTTGAC | AAAAAATATA | 4550 |
| CAGTCAAGGT | TTGAATCTAA | ATTAGAAATT | GTTGTGTCCA | ATGTTTTGAT | 4600 |
| TTTGATATTT | TATTCCTCTT | GTGAGACAAG | CTTATATATA | AATTATGATT | 4650 |
| TTTAATTCTA | AATTGGTTTG | GAGACATTAC | AAAAAGGCGT | TAATCTGCTG | 4700 |
| AAACTTAAAA | GATACAGCAG | CCTCAAGCTG | TCGTCTTAAA | AACAATCAGA | 4750 |
| ACATTATTAT | TCTAACTCCT | CAATTTGTCT | TGAAATTTCA | GGTTTGTGAT | 4800 |
| TTTGGTCTCT | CGCGATTGAA | GGCCAGCACG | TTTCTTTCCT | CGAAGTCAGC | 4850 |
| AGCTGGAACC | GTAAGTTCAG | TTTGTTTGAA | ACTAAACAC | GCTGAACAAC | 4900 |
| GTAACTTTCT | TCTAGGTCCT | ATTTCCAATG | GAAGCTAAAT | AATTACTGAC | 4950 |
| TTTGATATAT | CAGCCCGAGT | GGATGGCACC | AGAAGTCCTG | CGAGATGAGC | 5000 |
| CGTCTAATGA | AAAGTCAGAT | GTGTACAGCT | TCGGGGTCAT | CTTGTGGGAG | 5050 |
| CTTGCTACAT | TGCAACAACC | ATGGGGTAAC | TTAAATCCGG | CTCAGGTACT | 5100 |
| TCCCACTCTA | AACATCCCAA | ATAATAATGA | TATTATTTTG | CATTTGGAAG | 5150 |
| TCCCTCACTC | TACATTTCAT | AACATGCTAT | ATATGATCAT | CCAACAAAAT | 5200 |
| GTTCCATAGG | TTGTAGCTGC | GGTTGGTTTC | AAGTGTAAAC | GGCTGGAGAT | 5250 |
| CCCGCGTAAT | CTGAATCCTC | AGGTTGCAGC | CATAATCGAG | GGTTGTTGGA | 5300 |

-continued

| | | | | |
|---|---|---|---|---|
| CCAAGTACGT | TAAGATTTTC | TATCTCTTTT | TTGAATTCTT | CTTGAATAGA | 5350 |
| CTTCATGTTT | ATGTATGTGT | TTCATTACCA | GTGAGCCATG | GAAGCGTCCA | 5400 |
| TCATTTGCAA | CTATAATGGA | CTTGCTAAGA | CCATTGATCA | AATCAGCGGT | 5450 |
| TCCTCCGCCC | AACCGCTCGG | ATTTGTAAAA | TACCCCGGT | CCATTCAAAA | 5500 |
| GTTGTTATAA | TCATGATATG | CACATATACT | CTCAGCATTC | TTTTGCTGCC | 5550 |
| CAGGAGGGAG | ACACTAGTTA | AGATATAGCT | TTAAAGGTAC | ATTCCTCATG | 5600 |
| AGCTATCAAT | CATATCCTAC | AGAATCCCAT | GGTTTTTATA | CATGTATTAT | 5650 |
| TTTTGCGATC | TTTGTCTGCTG | TTTTGTTCC | CTTTTTAATG | TTGCAGATTG | 5700 |
| TTAAAATGTA | CATGACTATT | GTCACAGGGA | GGAAAAAAAA | ATGTAGTAAT | 5750 |
| GGAAACAATG | TGAGGGATAT | AATCTATCTA | TCTAGTCCCA | AAGGGTAAGC | 5800 |
| AATATTGTGT | TGTTATGTCT | TTGTAGCAAT | GCACTGAAAG | CTATATTTAA | 5850 |
| TTACATTGCT | GTACATTTAT | ACCGCTAAAT | TAGTTACTAA | GCGAAGGTAA | 5900 |
| AAAAGAGCAG | CTGGTAAATG | CTGTCAAAGG | GTTTTGCAAA | CTCAATATGA | 5950 |
| TTCATTGGAT | TTACATTTGT | TCACTGTGCG | ATTAGTCTGG | ACTATAAACC | 6000 |
| AACAGAAATG | AAATAAGACT | GTAACTTTCG | GAGACTCTAA | TACAGATGAA | 6050 |
| TATAATCCCA | AATCGTTAAA | AACGCATTGG | GACTGAAAAT | ATCTAGATAC | 6100 |
| ATAGTCAACT | ATTTTTGCCT | TCGCGTCTAA | GTAAGTTCCC | ACACTTGAAA | 6150 |
| ACGACTTTAC | CTGTCTTCCG | AATTAATCGT | TTGATGGATC | GGTAACCAAT | 6200 |
| AGGATTGCGT | AAATCAAAAT | TATACAATAT | TAAATTCTGA | AAAAGGAAAC | 6250 |
| ACGAAAAGCG | AATCAGTGAT | TTGTGAGGGC | CCAGTTCCAA | ATTAGAAAGC | 6300 |
| TGACCTGGCA | AA | | | | 6312 |

( 2 ) INFORMATION FOR SEQ ID NO:8:

( i ) SEQUENCE CHARACTERISTICS:
        ( A ) LENGTH: 13 amino acid residues
        ( B ) TYPE: amino acid
        ( C ) STRANDEDNESS:
        ( D ) TOPOLOGY: unknown ( i i ) MOLECULE TYPE:

( x i ) SEQUENCE DESCRIPTION: SEQ ID NO:8:

Ile Val His Arg Asp Leu Lys Ser Pro Asn Leu Leu Val
1               5                   10

( 2 ) INFORMATION FOR SEQ ID NO:9:

( i ) SEQUENCE CHARACTERISTICS:
        ( A ) LENGTH: 9 amino acid residues
        ( B ) TYPE: amino acid
        ( C ) STRANDEDNESS:
        ( D ) TOPOLOGY: unknown ( i i ) MOLECULE TYPE:

( x i ) SEQUENCE DESCRIPTION: SEQ ID NO:9:

Ile Gly Ala Gly Ser Phe Gly Thr Val
1               5

( 2 ) INFORMATION FOR SEQ ID NO:10:

( i ) SEQUENCE CHARACTERISTICS:
        ( A ) LENGTH: 8 amino acid residues
        ( B ) TYPE: amino acid
        ( C ) STRANDEDNESS:
        ( D ) TOPOLOGY: unknown (i i) MOLECULE TYPE:

(x i) SEQUENCE DESCRIPTION: SEQ ID NO:10:

His Arg Asp Leu Lys Ser Pro Asn
 1               5

(2) INFORMATION FOR SEQ ID NO:11:

(i) SEQUENCE CHARACTERISTICS:
        (A) LENGTH: 8 amino acid residues
        (B) TYPE: amino acid
        (C) STRANDEDNESS:
        (D) TOPOLOGY: unknown (i i) MOLECULE TYPE:

(x i) SEQUENCE DESCRIPTION: SEQ ID NO:11:

Thr Pro Glu Trp Met Ala Pro Glu
 1               5

(2) INFORMATION FOR SEQ ID NO:12:

(i) SEQUENCE CHARACTERISTICS:
        (A) LENGTH: 8 amino acid residues
        (B) TYPE: amino acid
        (C) STRANDEDNESS:
        (D) TOPOLOGY: unknown (i i) MOLECULE TYPE:

(x i) SEQUENCE DESCRIPTION: SEQ ID NO:12:

Gly Xaa Xaa Xaa Xaa Gly Lys Ser
 1               5

(2) INFORMATION FOR SEQ ID NO:13:

(i) SEQUENCE CHARACTERISTICS:
        (A) LENGTH: 8 amino acid residues
        (B) TYPE: amino acid
        (C) STRANDEDNESS:
        (D) TOPOLOGY: unknown (i i) MOLECULE TYPE:

(x i) SEQUENCE DESCRIPTION: SEQ ID NO:13:

Gly Xaa Xaa Xaa Xaa Gly Lys Thr
 1               5